(12) United States Patent  (10) Patent No.: US 9,134,245 B2
Jensen  (45) Date of Patent: *Sep. 15, 2015

(54) CELL-BASED ANTIOXIDANT PROTECTION ASSAY

(71) Applicant: Natural Immune Systems, Inc., Klamath Falls, OR (US)

(72) Inventor: Gitte S. Jensen, Klamath Falls, OR (US)

(73) Assignee: Natural Immune Systems, Inc., Klamath Falls, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/902,556

(22) Filed: May 24, 2013

(65) Prior Publication Data
US 2013/0260418 A1    Oct. 3, 2013

Related U.S. Application Data

(63) Continuation of application No. 12/740,776, filed as application No. PCT/US2008/082141 on Oct. 31, 2008, now Pat. No. 8,465,988.

(60) Provisional application No. 60/985,166, filed on Nov. 2, 2007.

(51) Int. Cl.
   *G01N 33/52*    (2006.01)
   *G01N 21/64*    (2006.01)
   *G01N 33/50*    (2006.01)

(52) U.S. Cl.
   CPC ........ *G01N 21/6486* (2013.01); *G01N 33/5014* (2013.01); *G01N 33/52* (2013.01); *Y10T 436/105831* (2015.01); *Y10T 436/13* (2015.01); *Y10T 436/25125* (2015.01); *Y10T 436/25375* (2015.01)

(58) Field of Classification Search
   USPC ............ 435/7.25, 40.5; 436/520, 522, 15, 56, 436/63, 66, 172, 173, 175, 177; 424/9.2
   See application file for complete search history.

(56) References Cited

U.S. PATENT DOCUMENTS

8,465,988 B2 *    6/2013   Jensen ......................... 436/522
2007/0021450 A1 *   1/2007   Sklarz et al. .................. 514/269

OTHER PUBLICATIONS

Lopez-Revuelta et al. Membrane cholesterol contents influence the protective effects of quercetin and rutin in erythrocytes damaged by oxidative stress, Chemico Biological Interaction, vol. 161, pp. 79-91 (2006).*

Grinberg et al., "N-acetylcysteine amide, a novel cell-permeating thiol, restores cellular glutathione and protects human red blood cells from oxidative stress," *Free Radical Biology and Medicine*, vol. 38, pp. 136-145, 2005.

Honzel et al., "Comparison of Chemical and Cell-Based Antioxidant Methods for Evaluation of Foods and Natural Products: Generating Multifaceted Data by Parallel Testing Using Erythrocytes and Polymorphonuclear Cells," *J. Agric. Food Chem.*, vol. 56, pp. 8319-8325, 2008.

(Continued)

*Primary Examiner* — Gail R Gabel

(74) *Attorney, Agent, or Firm* — Klarquist Sparkman, LLP

(57) ABSTRACT

Methods are provided herein for determining antioxidant activity of a test sample in intact cells. The method includes determining the antioxidant capacity of a test sample in intact red blood cells, wherein the test sample is added to intact red blood cells and oxidative damage is measured by alteration of fluorescence intensity of an oxidation-sensitive fluorescent indicator dye.

17 Claims, 13 Drawing Sheets

(56) References Cited

OTHER PUBLICATIONS

Jensen et al., "In Vitro and In Vivo Antioxidant and Anti-inflammatory Capacities of an Antioxidant-Rich Fruit and Berry Juice Blend. Results of a Pilot and Randomized, Double-Blinded, Placebo-Controlled, Crossover Study," *J. Agric. Food Chem.*, vol. 56, pp. 8326-8333, 2008.

Kusmic et al., "The antioxidant drug dipyridamole spares the vitamin E and thiols in red blood cells after oxidative stress," *Cardiovascular Research*, vol. 47, pp. 510-514, 2000.

Lopez-Revuelta et al., "Membrane cholesterol contents influence the protective effects of quercetin and rutin in erythrocytes damaged by oxidative stress," *Chemico Biological Interaction*, vol. 161, pp. 79-91, 2006.

Mitsuyama and May, "Uptake and antioxidant effects of ergothioneine in human erythrocytes," *Clinical Science*, vol. 97, pp. 407-411, 1999.

Zavodnik et al., "Melatonin directly scavenges free radicals generated in red blood cells and a cell-free system: Chemiluminescence measurements and theoretical calculations," *Life Sciences*, vol. 79, pp. 391-400, 2006.

\* cited by examiner

Flow cytometry assay

Whole cell CAP assay

CAP-e assay

Flow cytometry assay

Whole cell CAP assay

CAP-e assay

Flow cytometry assay

Whole cell CAP assay

CAP-e assay

CELL-BASED ANTIOXIDANT PROTECTION ASSAY

CROSS REFERENCE TO RELATED APPLICATIONS

This is a continuation of U.S. patent application Ser. No. 12/740,776, filed Apr. 30, 2010, now U.S. Pat. No. 8,465,988, issued Jun. 18, 2013, which is the §371 U.S. National Stage of International Application No. PCT/US2008/082141, filed Oct. 31, 2008, which was published in English under PCT Article 21(2), which in turn claims the benefit of U.S. Provisional Application No. 60/985,166, filed Nov. 2, 2007, all of which are incorporated herein by reference.

FIELD

This disclosure relates to the field of methods for determining the antioxidant activity of a test sample, particularly cell-based methods utilizing red blood cells.

BACKGROUND

Oxidative stress is a state that occurs when the generation of reactive oxygen species (ROS) exceeds a system's capacity to neutralize them. Similarly, nitrosative stress is a state that occurs when generation of reactive nitrogen species (RNS) exceeds the rate of neutralization. Oxidative and nitrosative stress are believed to play a role in aging and many diseases, including cardiovascular disease, cancer, inflammatory diseases, metabolic disease (such as diabetes), and neurodegenerative diseases.

Antioxidants are compounds which have the capacity to absorb and neutralize free radicals generated by ROS and RNS. These compounds can play an important role in the prevention or treatment of diseases which include a component of oxidative stress. As such, there is an increased focus on antioxidant levels in the diet and other products, such as nutritional supplements.

Standardized tests have been developed which measure antioxidant levels in nutritional and natural products, as well as in blood samples from a subject before and after consuming such products. One such assay is the non-cell based oxygen radical absorbance capacity assay (ORAC) (see Cao et al., Free Radic. Biol. Med. 14:303-311, 1993). In the ORAC assay, a test sample is incubated with a fluorescent indicator dye which is sensitive to oxidative damage and a free radical generator, and fluorescence intensity is measured. The result is expressed relative to the protection provided by the antioxidant standard TROLOX®. Another commonly used non-cell based method is the TROLOX® equivalent antioxidant capacity (TEAC) assay. In this assay, the formation of ferryl myoglobin radicals from metmyoglobin and hydrogen peroxide oxides 2,2'-azino-bis(3-ethylbenzthiazoline-6-sulfonic acid) (ATBS) to produce a radical cation which is chromogenic and can be detected at 405 nm (Miller et al., Biochem. Soc. Trans. 21:95 S, 1993). As with ORAC, the antioxidant activity of the test sample is expressed relative to the antioxidant activity of the standard TROLOX®. A drawback of these assays is that they do not provide information on the ability of the products tested to penetrate the cell membrane.

SUMMARY

Methods are disclosed herein for assessing the antioxidant activity of a test sample in red blood cells. In several embodiments, the method includes adding a test sample to intact red blood cells (RBC), washing away unabsorbed test sample, adding a fluorescent indicator dye which indicates oxidative stress, and detecting fluorescence intensity of the indicator. A decrease in fluorescence intensity, for example as compared with a control, indicates that the test sample has antioxidant activity. In some embodiments, the RBC are lysed following the addition of the sample and washing ways of unabsorbed sample. These methods can be performed in plates, such as for a high-throughput method.

In several embodiments, the fluorescent indicator dye becomes fluorescent upon exposure to reactive oxygen species. In additional embodiments, the fluorescent indicator dye becomes fluorescent upon exposure to reactive nitrogen species. In further embodiments, the method includes adding a free radical generator in the presence of the fluorescent indicator dye.

In several embodiments, the test sample comprises a compound of interest, such as a food or beverage, an extract, a purified compound, or serum from a subject. In some examples, the test sample includes standards with known antioxidant activity.

In additional embodiments, the method includes administering a test sample to a subject, collecting RBC from the subject, lysing the RBC, adding a fluorescent indicator dye which indicates oxidative stress, and detecting fluorescence intensity. In some examples, the method includes adding a free radical generator in the presence of the fluorescent indicator dye. In particular examples, RBC are collected from a subject before and after administration of a test sample.

The foregoing and other objects, features, and advantages of the invention will become more apparent from the following detailed description, which proceeds with reference to the accompanying figures.

BRIEF DESCRIPTION OF THE DRAWINGS

FIG. 7 is a series of graphs showing the percent inhibition of oxidative damage generated by H2O2 challenge in RBC treated with gallic acid (GA).

FIG. 8 is a series of graphs showing the percent inhibition of oxidative damage generated by H2O2 in RBC treated with a test sample containing hyaluronic acid and methyl sulfonyl methane.

FIG. 9 is a series of graphs showing the percent inhibition of oxidative damage generated by H2O2 in RBC treated with a test sample containing a fruit juice.

DETAILED DESCRIPTION

I. Abbreviations

Figure 1:
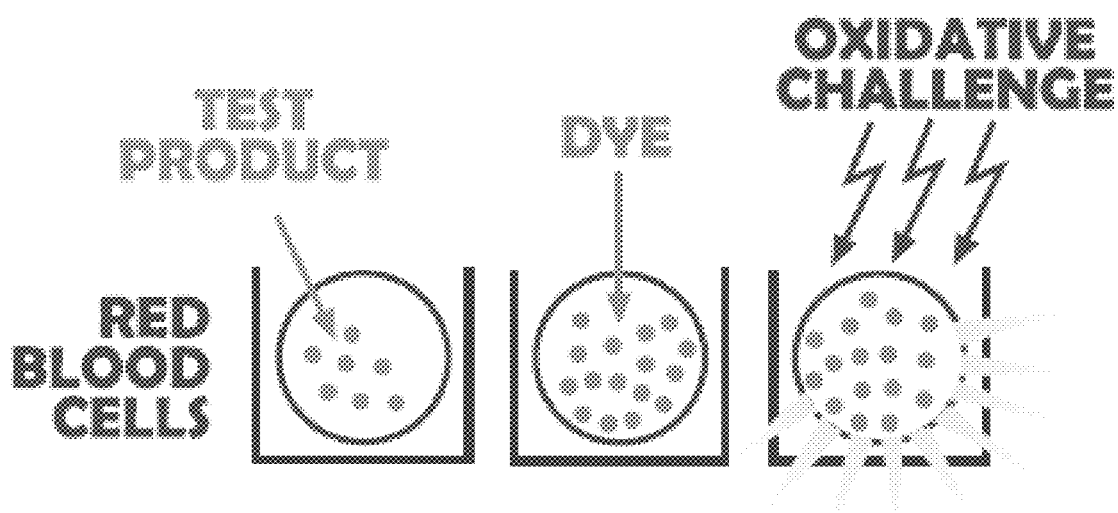
FIG. 1 is a schematic representation of the CAP-e assay method. Intact RBC are treated with a test product (test sample) to allow absorption into the cells, followed by washing to remove unabsorbed test product (test sample). A fluorescent indicator dye which measures oxidative stress is added and an oxidative challenge is created by adding a free radical generator. Fluorescence intensity is measured using a microplate reader. Alternatively, the RBC can be lysed prior to the addition of the fluorescent indicator dye.

AAPH: 2,2'-azobis(2-amidinopropane) dihydrochloride
CAP: cell-based antioxidant protection assay
CAP-e: cell-based antioxidant protection assay in erythrocytes
CM-H2DCFDA: 5-(and-6)-chloromethyl-2',7'-dichlorodihydrofluorescein diacetate acetyl ester
DAF-FM: 4-amino-5-methylamino-2',7'-difluorofluorescein
DCF-DA: 2',7'-dichlorodihydrofluorescein diacetate
GA: gallic acid
Hb: hemoglobin
MSM: methyl sulfonyl methane
ORAC: oxygen radical absorbance capacity
PBS: phosphate-buffered saline
PS: physiological saline
RBC: red blood cell
RNS: reactive nitrogen species
ROS: reactive oxygen species II. Terms Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Definitions and additional information known to one of skill in the art in immunology can be found, for example, in Fundamental Immunology, W. E. Paul, ed., fourth edition, Lippincott-Raven Publishers, 1999.

In order to facilitate review of the various embodiments of this disclosure, the following explanations of specific terms are provided:

Antioxidant: A substance that, when present in a mixture or structure containing an oxidizable substrate molecule (e.g., an oxidizable biological molecule or oxidizable indicator), significantly delays or prevents oxidation of the oxidizable substrate molecule. Antioxidants can act by scavenging biologically important reactive free radicals or other ROS or RNS, or by preventing their formation, or by catalytically converting the free radical or other ROS or RNS to a less reactive species. Cells have endogenous antioxidant machinery, which includes enzymes (such as superoxide dismutase, catalase, and glutathione peroxidase) and proteins (such as albumin, metallothionine, transferrin, ceruloplasmin, myoglobin, and ferritin). Additional antioxidants include compounds such as carotenoids (such as lutein, zeaxanthin, β-cryptoxanthin, lycopene, α-carotene, and β-carotene), tocopherols (such as vitamin E, α-tocopherol, γ-tocopherol, and δ-tocopherol), retinoids (such as vitamin A, retinol, and retinyl palmitate), and fat-soluble polyphenols such as quercetin. Antioxidants also include compounds such as ascorbic acid (vitamin C) and its oxidized form dehydroascorbic acid, uric acid and its oxidized form allantoin, bilirubin, albumin, isoflavones, procyanidins, and water-soluble polyphenols such as catechins.

Antioxidant activity: The ability of a compound to inhibit oxidative damage caused by free radicals or other ROS or RNS. The antioxidant activity of a test sample may be expressed relative to a known antioxidant, for example as TROLOX® equivalents (see, e.g., U.S. Pat. No. 7,132,296). The antioxidant activity of a compound may also be expressed as a percentage inhibition of oxidative damage, where oxidative damage is assessed by use of an indicator dye which becomes fluorescent upon oxidative damage (such as under conditions of oxidative stress).

Compound of interest: A compound which potentially exhibits antioxidant activity. The compound can be an organic compound. The compound can be a vitamin, such as vitamin E or vitamin C. The compound can be synthesized or purified, such as gallic acid, hyaluronic acid, methyl sulfonyl methane (MSM), phycocyanin, or sugars. The compound may also be contained in a mixture, such as an extract (from plant, animal, or other biological materials), food (such as cooked food, raw food, baked goods, milk products, meat products, or spices), or beverages (such as teas, soft drinks, milk, juices, or flavored waters).

Extract: A substance obtained from a mixture by a physical or chemical process, for example by dissolving the substance in a solvent. An extract includes an organic product derived from a biological material, such as a fruit, vegetable, plant, or animal material. The process of generating an extract may include the use of solvents, such as aqueous solvents (for example physiological saline, water, 1-4% glucose, or 1-4% fructose), organic solvents (for example, ethanol, methanol, acetone, glycerol, acetonitrile, dimethyl sulfoxide, or PLURONIC® surfactants), or combinations thereof. Preparation of an extract may also include treatment of the starting material with heat or pressure. Extracts may also be prepared by mechanical means, such as grinding, sonication, or freeze-thaw treatment.

Flow cytometry: A method for detecting fluorescence intensity of stained cells. Cells are labeled with a fluorescent dye and then passed, in suspending medium, through a narrow nozzle so that each cell passes the detector in single file. A laser based detector system is used to excite fluorescence and a series of photocells measure physical characteristics as well as fluorescence intensity of each cell. The machine can be used either as an analytical tool, counting the number of labeled cells in a population, or to separate the cells for subsequent growth of the selected population. A second laser system can be included to expand the number of dyes that can be detected simultaneously on each cell. Flow cytometry examines large numbers of individual cells and fluorescence activated cell sorting (FACS) makes possible the separation of populations of cells.

Fluorescence intensity: The amount of fluorescence emitted from a fluorescent molecule, such as an intrinsically fluorescent molecule (for example fluorescein, dichlorodihydrofluorescein, 4-amino-5-methylamino-2',7'-difluorofluorescein diacetate, β-phycoerythrin, dihydroethidium, dihyrorhodamine 123, and dihydrocalcein, among others) or a fluorophore complexed to a protein or nucleic acid. Fluorescence detection methods suitable for use in the method of the present invention include conventional fluorometry, fluorescence microscopy, flow cytometry and fluorescence spectroscopy. For high throughput screening, laser scanning imaging and microplate fluorescence readers are suitable.

Fluorescent indicator dye: A compound that interacts with a free radical and becomes oxidized and which exhibits oxidation-sensitive changes in fluorescence. The fluorescent indicator dyes for use in the described assays indicate oxidative stress, for example by measuring oxidation of the dye by free radicals. The change in state of the indicator can be monitored directly by measurement of fluorescence intensity. Examples of fluorescent indicator dyes that measure oxidative stress include, but are not limited to, fluorescein, dichlorodihydrofluorescein, 4-amino-5-methylamino-2',7'-difluorofluorescein diacetate, β-phycoerythrin, dihydroethidium, dihyrorhodamine 123, and dihydrocalcein, among others. Hemoglobin, which is endogenous to RBC, exhibits altered fluorescence in response to oxidation, and is also an example of a fluorescent indicator dye which measures oxidative stress.

Free radical: A chemically reactive species which possesses one or more single unpaired electrons. Free radicals include reactive oxygen species and reactive nitrogen species. In cells, free radicals cause oxidative damage, for example to lipids, proteins, or nucleic acids.

Free radicals arise during normal metabolism as a consequence of ATP production by the mitochondria. They are also generated by neutrophils and other cell types as part of inflammatory processes. Environmental factors, such as ionizing radiation, pollution, environmental toxins, and lifestyle stressors, such as cigarette smoking and alcohol consumption also affect levels of free radicals.

A free radical generator is a compound which produces ROS or RNS. Examples of free radical generators include hydrogen peroxide, 2,2'-azobis(2-amidinopropane) dihydrochloride (AAPH), tert-butylhydroperoxide, and cumene hydroperoxide.

Hemoglobin (Hb): An iron-containing metalloprotein located in the RBC of vertebrates and other animals which functions to transport oxygen and carbon dioxide in the blood. Vertebrate Hb consists of four polypeptide chains, each containing an iron-containing heme group. In adults, the principal Hb (HbA) consists of two α chains and two β chains. A minor Hb form (HbA2) also occurs in adults, consisting of two α chains and two δ chains. The major Hb during fetal development is HbF, which contains two α chains and two γ chains.

Oxidative challenge (oxidative stress): Conditions under which molecules such as lipids, proteins, or nucleic acids are vulnerable to oxidative damage. An oxidative challenge can involve the introduction of free radicals, ROS, or RNS, such as to RBC or lysed RBC, for example in an assay of antioxidant activity. The oxidative challenge may be created by adding a free radical generator, such as hydrogen peroxide or AAPH.

Oxidative damage: Damage to cellular components, such as lipids, proteins, or nucleic acids from oxidation or nitrosylation resulting from the presence of free radicals, ROS, or RNS. Oxidative damage may contribute to disease states, such as cardiovascular disease (for example atherosclerosis, ischemia/reperfusion injury, restenosis, and hypertension), cancer, inflammatory diseases (such as acute respiratory distress syndrome, asthma, inflammatory bowel disease, dermal and ocular inflammation, and arthritis), metabolic disease such as diabetes, and diseases of the central nervous system such as amyotrophic lateral sclerosis, Alzheimer disease, Parkinson disease, or stroke.

The lipid components of the cell membrane are prone to oxidative damage. ROS species act on unsaturated lipids to yield reactive unsaturated aldehydes. These unsaturated aldehydes can react with other cellular components, such as membrane-bound or associated proteins and nucleic acids, thereby crosslinking them to the lipid. Oxidized lipids may be identified by presence of lipid peroxides.

Proteins are also susceptible to oxidative damage. In particular, proteins containing sulfhydryl groups and iron-sulfur clusters are vulnerable to attack by ROS. For example, ROS attack on mitochondrial aconitase will cause release of the iron from the protein and inactivation of the enzyme. Oxidative damage to proteins may inhibit normal function, induce protein fragmentation, or lead to crosslinking with lipids, nucleic acids and other proteins, promoting formation of aggregates. Oxidized proteins may be identified by presence of protein carbonyls.

Oxidative damage to nucleic acids results in strand breakage and formation of abasic sites, oxidized bases and DNA adducts. Damaged bases can lead to mutations or altered gene expression. Oxidized nucleic acids may be identified by presence of oxidized bases, such as 8-oxo-guanine.

Physiological saline (PS): A solution which contains a physiological concentration of saline (about 0.85-0.9%), such as 0.9% NaCl. In some examples, the PS may be buffered. Examples of buffered PS include phosphate-buffered saline (PBS), Hank's balanced salt solution, or lactated Ringer's solution. PS may also contain electrolytes other than sodium, such as potassium, chloride, calcium and phosphate.

Reactive Nitrogen Species: Radical nitrogen-based molecules which can facilitate nitrosylation reactions. RNS include peroxynitrite (OONO—), peroxynitrous acid (ONOOH), nitroxyl anion (NO—), nitryl chloride ($NO_2Cl$), nitrosyl cation (NO+), nitrogen dioxide ($NO_2$.), dinitrogen trioxide ($N_2O_3$), and nitrous acid ($HNO_2$).

Reactive Oxygen Species: Radical and non-radical reactive oxygen derivatives, which may participate in reactions that give rise to free radicals. Radical ROS include hydroxyl radical (OH.), superoxide radical ($O_2$.-), nitric oxide (NO.), thyl (RS.), peroxyl ($RO_2$.), and lipid peroxyl (LOO.). Non-radical ROS include peroxynitrite (ONOO—), hypochloric acid (HOCl), hydrogen peroxide (H2O2), singlet oxygen, ozone (O3), and lipid peroxide (LOOH).

Red Blood Cell: Erythrocytes (red blood cells) are cells specializing in the delivery of oxygen and nitric oxide to peripheral tissue, where these compounds are exchanged for carbon dioxide, for transport to the lungs. RBC are living, energy-producing cells, and represent the most abundant cell type in the marrow and the blood circulation, where they outnumber white blood cells by at least 100-fold. RBC are produced from stem cells in the bone marrow, and their final stages of maturation before entering the blood circulation involve packing of the cytoplasm with hemoglobin and redox enzymes and expelling of the nucleus and organelles (such as mitochondria) in humans and other mammals, but not in birds or reptiles. Despite the lack of mitochondria in the mature mammalian RBC, the cell is still capable of producing ATP as a source of energy, primarily based on glycolysis. Mature RBC survive in the blood circulation for approximately 120 days, after which time they are cleared in the spleen. A "red blood cell lysate" is a mixture of substances formed by the lysis of RBC. The lysate includes for example, RBC cell membranes, Hb, and the other cellular components of RBC. The RBC lysate also includes the buffer or other liquid in which the lysis was performed.

Sample: A sample or "test sample" includes a liquid or solid which contains at least one compound of interest which may have antioxidant activity. Samples include isolated or purified compounds of interest, such as vitamins (for example, vitamin E and vitamin C), gallic acid, hyaluronic acid, MSM, phycocyanin, chlorophyll and derivatives, sugars, isolated milk peptides, xanthones, anthocyanins, and purified flavones and flavonoids (such as those from fruits and chocolate). A sample may be a biological sample, such as blood, serum, plasma, plant products (for example, leaves, flowers, seeds, fruits, or vegetables), or animal products (such as meat, milk, colostrum, eggs, or cartilage). Samples also include extracts, such as an extract from a biological sample, for example fruit (such as berries, grapes, apples, citrus fruits, bananas, cherries, or mangosteen), vegetable (such as broccoli, carrots, or leafy greens), mushrooms (such as morel, shiitake, reishi, chanterelle, or cordyceps), yeast (such as *Saccharomyces cerevisiae*), cyanobacteria (such as spirulina), green algae (such as *Chlorella*), brown algae (such as Fucus), milk, colostrum, or cartilage. Samples may also include foods, such as cooked food, raw food (for example, egg products or raw egg fractions), baked goods (for example, breads, cookies, or granola bars), meat products (raw or cooked), or soups; beverages, such as tea, soft drink, flavored water, milk or milk products, juice, or cocoa; or spices, such as cinnamon, cloves, cocoa powder, or dried herbs (such as oregano).

Sensitivity: The sensitivity of an assay describes the smallest amount of a substance or characteristic that can be measured by an assay. It may also describe the change in the response of a system for a small change of the stimulus causing the response, i.e., the ratio of the response of a system to the stimulus causing it. For example, the sensitivity of an assay which measures antioxidant activity of a test sample may be related to its ability to detect an inhibition of oxidative damage at a lower dose of a test sample than another assay method. In another example, the sensitivity of an assay may be related to its ability to detect a greater magnitude of response to the same concentration of stimulus than another assay method.

In contrast, "specificity" refers to the ability of a test to detect antioxidant activity, as compared to other enzymatic activities.

Subject: Living multi-cellular vertebrate organisms, a category that includes human and non-human mammals (such as laboratory or veterinary subjects), birds (such as poultry), fish, amphibians, or reptiles.

There is a growing recognition of the role of red blood cells (RBC) in cellular signaling beyond their oxygen-transporting function (Buehler and Alayash, Antioxid. Redox. Signal. 7:1755-1760, 2005). During their life in the circulation RBC have important protective functions far beyond the transport of oxygen, nitric oxide, and carbon dioxide. They provide physical and antioxidant protection for leukocyte subsets such as polymorphonuclear leukocytes, and also inhibit inflammation by de-activating leukocytes by inhibiting pseudopod formation and endothelial adhesion (Komai and Schmid-Schonbein, Ann. Biomed. Eng. 33:1375-1386, 2005).

The ability of RBC to scavenge reactive oxygen and nitrogen species represents direct antioxidant and anti-inflammatory protection of the body. The redox enzymes found in RBC include glutathione, superoxide dismutase, catalase, glutathione peroxidase, glutathione S-transferase, and glucose-6-phosphate dehydrogenase. In addition, the plasma membrane oxidoreductase serves as a major mechanism of extracellular oxidants, and may be important mechanism for maintaining a reduced environment in the blood plasma (Fiorani and Accorsi, Br. J. Nutr. 94:338-345, 2005).

The antioxidant status of RBC is recognized as a clinically meaningful biological indicator of progression of acute and chronic disease states involving oxidative stress (Minetti and Malorni, Antioxid. Redox Signal. 8:1165-1169, 2006). An increasing number of methods involve RBC to evaluate oxidative damage as a result of inflammation, as well as antioxidant protection by natural products. Some methods focus on lipid peroxidation, using either intact RBC or RBC membranes for measuring malondialdehyde, an indicator of lipid peroxidation (Gawlik and Czajka, Acta Pol. Pharm. 64:159-164, 2007; Lam et al., J. Am. Coll. Nutr. 26:233-242, 2007). Other laboratories focus on the levels of redox enzymes, such as superoxide dismutase, catalase, or glutathione peroxidase (Bednarek-Tupikowska et al., Clin. Endocrinol. (Oxf.) 64:463-468, 2006; Lexis et al., Am. J. Transpl. 6:41-49, 2006). Multiple laboratories evaluate oxidative damage in RBC by measuring hemolysis of the cells (Li et al., J. Pharm. Pharmacol. 59:739-743, 2007; Lam et al., supra; Yang et al., Food Chem. Toxicol. 44:1513-1521, 2006; Dai et al., Life Sci. 78:2488-2493, 2006). However, these assays are time-consuming and have other drawbacks. For example, these assays are focused on detecting lipid peroxidation in RBC membranes. The assays also do not address whether the antioxidant candidate compound is able to cross the cell membrane. There is a need for improved, rapid cell-based assays which can measure protection from both hydroxyl and peroxyl free radicals by compounds which can enter cells under physiological conditions.

Described herein are assays for detecting the antioxidant activity of a test sample using RBC. These assays provide a rapid method that can be used in a high-throughput format and do not rely on assaying for the presence of a specific enzyme.

Methods for Determining Antioxidant Activity of a Sample

Methods are provided herein for determining the antioxidant activity of a test sample. In several embodiments, intact RBC are treated with a test sample to allow absorption into the cells, followed by washing to remove unabsorbed test sample. A fluorescent indicator dye which indicates oxidative stress is added and an oxidative challenge is created by adding a free radical generator. Fluorescence intensity is measured using a microplate reader. The method is shown in FIG. 1. Alternatively, the RBC can be lysed prior to the addition of the fluorescent indicator dye. In particular examples, the fluorescence intensity is not measured by flow cytometry. In some examples, the fluorescence intensity is detected using a microplate reader.

In several embodiments, the method includes adding a test sample to intact RBC, washing the RBC to remove any unabsorbed test sample, lysing the RBC, adding a fluorescent indicator dye which indicates oxidative stress to the lysed cells, and detecting fluorescence intensity. The method includes detecting fluorescence intensity of the indicator dye following treatment of RBC with the test sample or a control, such that a decrease in fluorescence intensity following treatment of RBC with the test sample as compared to the control indicates that the test sample contains antioxidants. In some examples the control includes RBC which have not been treated with any test sample.

In particular embodiments, the RBC are isolated from a subject of interest, such as a subject who has ingested a specific substance. The RBC can be isolated from blood from any subject, including veterinary and human subjects. A subject includes any living multi-cellular vertebrate organism, a category that includes human and non-human mammals (such as laboratory or veterinary subjects, for example, cows, sheep, horses, dogs, or cats), birds (such as poultry, for example chicken or turkey), fish, reptiles, and amphibians. In some examples, the RBC are isolated from a subject who does not have an underlying disease (such as cardiovascular disease (for example atherosclerosis, ischemia/reperfusion injury, restenosis, and hypertension), cancer, inflammatory diseases (such as acute respiratory distress syndrome, asthma, inflammatory bowel disease, dermal and ocular inflammation, and arthritis), metabolic disease such as diabetes, and diseases of the central nervous system such as amyotrophic lateral sclerosis, Alzheimer disease, Parkinson disease, or stroke).

The RBC can be isolated from blood and other bodily fluids collected for any reason, such as for a blood donation or post-operative drain. RBC can be isolated from blood, such as by density gradient centrifugation. The isolated RBC can be washed to remove serum components, for example using a physiological buffer, such as 0.9% saline. In some examples, freshly prepared RBC are used in the disclosed methods. In other examples, the RBC are stored at 4° C. prior to use in the disclosed methods (such as for about 1 day to about 20 weeks, for example about 1 week to about 16 weeks, about 2 weeks to about 10 weeks, or about 4 weeks to about 8 weeks). In particular examples, RBC stored at 4° C. for about 4-8 weeks are used for testing the antioxidant activity of a test sample.

In additional embodiments, the RBC are exposed to an oxidative challenge, such as by treatment with a compound that is a free radical generator. In particular examples, the free radical generator is added in the presence of a fluorescent indicator dye which measures oxidative stress. The method includes detecting fluorescence intensity of an indicator dye in the presence of a free radical generator following incubation with a test sample or a control, such that a decrease in fluorescence intensity indicates that the test sample has antioxidant activity. In some examples, the control includes RBC which have been exposed to oxidative challenge, but which have not been exposed to any test sample.

In another embodiment, the method includes adding a test sample to intact RBC, washing the RBC to remove unabsorbed test sample, lysing the RBC, and detecting fluorescence intensity. The fluorescence is generated by the hemoglobin (Hb) which is endogenous to the RBC. The method includes detecting fluorescence intensity of Hb in following treatment of the RBC with the test sample and following treatment of RBC with a control, such that a decrease in fluorescence intensity following treatment with the test sample as compared to the control indicates that the test sample has antioxidant activity. In some examples the control includes RBC which have not been treated with any test sample.

In further embodiments, the RBC are exposed to an oxidative challenge, such as by treatment with a compound that is a free radical generator. In particular examples, the free radical generator is added in the presence of the lysed RBC. The method includes detecting fluorescence intensity of Hb in the presence of a free radical generator in the presence of a test sample and in the presence of a control, such that a decrease in fluorescence intensity indicates that the test sample has antioxidant activity. In some examples, the control includes RBC which have been exposed to an oxidative challenge, but which have not been exposed to any test sample.

In some examples, the assay is carried out in microplates, such as 24-well, 48-well, 96-well or 384-well microtiter plates. In several embodiments, the fluorescence intensity is detected using a microplate reader. A microplate reader is a laboratory instrument designed to detect biological, chemical or physical events in microtiter plates. A high-intensity lamp passes light to the microtiter well and the light emitted by the reaction in the well is quantified by a detector. Detection modes for microplate assays include absorbance, fluorescence intensity, luminescence, time-resolved fluorescence, and fluorescence polarization. In particular embodiments, the fluorescence intensity is measured using a microplate reader, such as SPECTRAMAX® M5 (Molecular Devices), ELX800™ Absorbance Microplate Reader (BioTek), SpectraFluor (Tecan), or VICTOR3™ (Perkin Elmer). In several embodiments, the wavelength of light used for excitation is from about 485 nm to about 510 nm, such as about 485 nm to about 505 nm, such as about 495 nm to about 500 nm. The emitted light is detected at about 520 nm to about 560 nm, such as about 530 nm to about 550 nm, such as about 535 nm to about 540 nm. In a particular example, fluorescence intensity is measured using a Tecan SpectraFluor microplate reader using excitation at 485 nm and measuring emission at 535 nm.

In some embodiments, the method includes maintaining intact RBC throughout the assay. In one embodiment, the method includes adding a test sample to intact RBC, washing the RBC to remove any unabsorbed test sample, adding a fluorescent indicator dye that indicates oxidative stress and which is cell-permeable to the intact RBC, and detecting fluorescence intensity using a microplate reader. In another embodiment, the method includes adding a test sample to intact RBC, washing the RBC to remove any unabsorbed test sample, adding a fluorescent indicator dye that measures oxidative stress and which is cell-permeable to the intact RBC, adding a free radical generator, and detecting fluorescence intensity using a microplate reader.

When performed in small volumes, such as in a microplate, the methods provided herein provide advantages over a flow cytometry method, which requires maintaining intact cells throughout the assay. In several embodiments, the assays described herein are performed in a microplate, and flow cytometry analysis is not used. One advantage of the method is that substantially less time is required to perform the assay than using methods that require flow cytometry. In some embodiments, the methods disclosed herein can be performed in about one hour to about four hours, such as about two hours to about three hours. In contrast, the flow cytometry method typically requires about eight to nine hours to perform.

The methods provided have increased sensitivity for detection of antioxidant activity. For example, detectable fluorescence intensity is up to three orders of magnitude greater in assays utilizing a microplate reader to measure fluorescence as opposed to the flow cytometry method, such as about 10-fold to about 1000-fold greater, about 50-fold to about 500-fold greater, or about 100-fold to about 250-fold greater fluorescence intensity.

In some examples, the methods disclosed herein also exhibit a higher sensitivity for measuring antioxidant activity of a test sample than methods which maintain intact RBC throughout the assay. For example, no interference is observed in the methods utilizing lysed RBC with high concentrations of test sample (such as greater than about 10 mg/ml test sample), while interference occurs in whole cell microplate assays above about 6 mg/ml test sample and in flow cytometry assays above about 1 mg/ml test sample. The methods herein also generate more linear dose response curves for test samples than do methods which maintain intact RBC throughout the assay.

In one embodiment, the method includes lysing RBC, adding a fluorescent indicator dye which indicates oxidative stress, and detecting fluorescence intensity. The method includes detecting fluorescence intensity of the indicator dye in RBC from a subject and detecting fluorescence intensity of the indicator dye in RBC from a control population, such that the amount of antioxidant activity is the inherent antioxidant protection of the RBC from the subject. In some examples, a free radical generator is added to the RBC in the presence of the fluorescent indicator dye.

In some embodiments, the method includes determining antioxidant activity of a test sample by administering a test sample to a subject, collecting RBC from the subject, lysing the RBC, adding a fluorescent indicator dye which indicates oxidative stress to the lysed RBC, and detecting fluorescence intensity, such as in a microplate. In some examples, a free radical generator is added in the presence of the fluorescent indicator dye. The method includes detecting fluorescence intensity following the administration of a test sample and detecting fluorescence intensity prior to administration of a test sample. A decrease in fluorescence intensity following administration of the test sample as compared to a control, such as fluorescence intensity prior to administration of the test sample or fluorescence intensity in RBC from a different subject who was not administered the test sample, indicates that the test sample has antioxidant activity.

In some examples, the method includes determining antioxidant activity in RBC prepared from subjects after consuming a test sample, such as a food, beverage, fruit (fresh or dried fruit, or fruit juice), vitamin supplement (such as vitamin C or vitamin E), extract (such as a colostrum-based extract), or algae (such as blue-green algae). The test sample may be administered to a fasting subject or fed to the subject with a test meal. In some embodiments the RBC are prepared from a subject, where blood is collected before and after the subject consumes a test sample. In some examples, the RBC are isolated from a subject who has ingested a test sample who does not have an underlying disease (such as cardiovascular disease (for example atherosclerosis, ischemia/reperfusion injury, restenosis, and hypertension), cancer, inflammatory diseases (such as acute respiratory distress syndrome, asthma, inflammatory bowel disease, dermal and ocular inflammation, and arthritis), metabolic disease such as diabetes, and diseases of the central nervous system such as amyotrophic lateral sclerosis, Alzheimer disease, Parkinson disease, or stroke). The antioxidant activity of RBC prepared from a subject after consuming a test sample can be compared to antioxidant activity of RBC prepared from the subject prior to consuming the test sample or RBC prepared from subjects which have not consumed the test sample.

In some examples, the method includes RBC prepared from subjects of increasing age, such as about 18 years old to about 110 years old, such as about 25 years old to about 100 years old, about 30 years old to about 90 years old, about 40 years old to about 80 years old, or about 50 years old to about 70 years old.

In several embodiments, the method includes adding a test sample to intact RBC. The test sample is incubated with the intact RBC for an amount of time to permit the molecules to enter the RBC. The test sample may be incubated with the RBC from about 1 to about 120 minutes, such as from about 10 minutes to about 100 minutes, about 20 minutes to about 90 minutes, about 30 minutes to about 80 minutes, about 40 minutes to about 70 minutes, about 50 minutes to about 60 minutes, such as at least about five minutes, for example about 5 minutes, 10 minutes, 15 minutes, 20 minutes, 30 minutes, 60 minutes, 90 minutes, or 120 minutes. The incubation is carried out at a temperature which permits the test sample to cross the RBC cell membrane. For example, the incubation of the test sample with the intact RBC may be at about room temperature, such as at a temperature of about 20° C. to about 25° C. In additional embodiments, the RBC are incubated at a temperature of about 4° C. to about 56° C., such as about 15° C. to about 50° C., about 22° C. to about 45° C., about 25° C. to about 40° C., or about 30° C. to about 37° C. In a particular example, the test sample is incubated with intact RBC for 20 minutes at room temperature.

In some embodiments, the RBC are washed following incubation with the test sample to remove any test sample material which has not crossed the cell membrane. Washing may be by standard methods, for example by centrifugation of the cells, removal of the resulting supernatant, and resuspension of the cells in a solution. The cells may be resuspended in a physiological buffer, such as phosphate-buffered saline, Hank's balanced salt solution, lactated Ringer's solution, or cell culture media (for example RPMI-1640). The buffers may contain small amounts of solvent (such as about 0.5% to about 2% ethanol or methanol) or carrier molecules (such as about 1% to about 4% glucose or fructose). The wash step may be repeated one to six times, such as one time, two times, three times, four times, five times, or six times. In a particular example, the RBC are washed three times by centrifugation at about 400×g for about 2 to about 10 minutes, removal of the resulting supernatant, and resuspension in phosphate buffered saline.

In several embodiments, the RBC are lysed following incubation with a test sample and washing. Lysis of the RBC may be by any conventional method, such as by hypotonic conditions, detergents, or physical disruption. Lysis of cells may be carried out by incubation under hypotonic conditions, for example by incubation of the cells in water, or a lysis buffer (such as a buffer containing 40 mM HEPES, 40 mM NaCl, 10 mM EDTA or a solution containing 0.8% NH4Cl). Cells may be lysed using detergents, for example by use of a buffer containing CHAPS, TRITON® X-100, sodium dodecyl sulfate, or NONIDET® P-40. Cells may also be lysed by physical disruption, such as by mechanical disruption (for example using a blender or polytron), liquid homogenization (for example by a dounce homogenizer or french press), sonication, freeze/thaw cycles, or manual grinding (for example using a mortar and pestle). In a particular example, RBC are lysed by incubating for 5 minutes in water at room temperature. The lysed RBC membranes ("ghosts") may be washed to remove the intracellular components, such as hemoglobin.

Fluorescent Indicators

In several embodiments, the method includes adding a fluorescent indicator dye which indicates or measures oxidative stress to determine antioxidant activity of the test sample. The fluorescent indicator dyes for use in the disclosed assays become oxidized in the presence of free radicals and exhibit oxidation-sensitive changes in fluorescence, thereby indicating oxidative stress, such as the presence of free radicals (for example ROS or RNS).

In some embodiments, the fluorescent indicator dye which indicates oxidative stress is added to the lysed RBC, following treatment with a test sample. The lysed cell mixture is incubated with the fluorescent indicator dye prior to detection of fluorescence intensity, such as for at least about 1 minute to about 6 hours, about 15 minutes to 4 hours, about 30 minutes to about 2 hours, about 1 hour to 1.5 hours, for example about 5 minutes, 10 minutes, 15 minutes, 20 minutes, 30 minutes, 1 hour, 1.5 hours, 2 hours, 3, hours, 4 hours, 5 hours, or 6 hours. In one example, fluorescence intensity is detected at a single time point. In another example, fluorescence intensity is measured over time, such as about once per minute for about 5 minutes to about 1 hour.

In additional embodiments, the RBC are not lysed, and a fluorescent indicator dye which indicates oxidative stress and which is capable of crossing the cell membrane is added to intact RBC following treatment with a test sample and washing. In one example, the intact RBC are incubated with a cell-permeable fluorescent indicator dye for about 1 minute to about 120 minutes, such as about 10 minutes to about 100 minutes, about 20 minutes to about 90 minutes, about 30 minutes to about 80 minutes, about 40 minutes to about 70 minutes, or about 50 minutes to about 60 minutes.

Fluorescent indicator dyes are probes which exhibit oxidation-sensitive changes in fluorescence, thereby measuring oxidative stress. The extent of oxidation of the fluorescent indicator dye is determined by measuring fluorescence intensity at a wavelength appropriate for the indicator used. The presence of an antioxidant compound reduces or prevents the oxidation of the indicator dye and decreases the change in fluorescence intensity caused by oxidation.

In some examples, the fluorescent indicator dye is used at a concentration of about 0.5 µM to about 1 mM, such as about 1 µM to about 0.9 mM, about 10 µM to about 0.8 mM, about 0.1 mM to about 0.7 mM, about 0.25 mM to about 0.6 mM, or about 0.4 mM to about 0.6 mM. In particular examples, the fluorescent indicator dye is used at concentrations of about 0.5 µM to about 20 µM.

Examples of fluorescent indicator dyes which measure oxidative stress for use in an assay for determining antioxidant activity include fluorescein and fluorescein derivatives, such as fluorescein, 3'(p-aminophenyl) fluorescein (APF), 3-(p-hydroxyphenyl) fluorescein (HPF), 2',7'-dichlorofluorescein (DCF), 2',7'-dichlorodihydrofluorescein (H2DCF), 2',7'-dichlorodihydrofluorescein diacetate (H2DCFDA), carboxylated H2DCFDA (carboxy-H2DCFDA), 5-(and 6-)-chloromethyl-2',7'-dichlorodihydrofluorescein diacetate, acetyl ester (CM-H2DCFDA), 2',7'-difluorodihydrofluorescein diacetate (DFF-DA), 5-(and 6-)-carboxy-2',7'-difluorodihydrofluorescein diacetate (carboxy-H2DFFDA), 4-amino-5-methylamino-2',7'-difluorofluorescein (DAF-FM), and DAF-FM diacetate.

Further examples of fluorescent indicator dyes for use in assessing antioxidant activity include rhodamines, such as rhodamine, dihydrorhodamine 123, dihydrorhodamine 6G, and diaminorhodamine-4M (DAR-4M). Additional fluorescent indicator dyes include dihydroethidium, dihydrocalcein, β-phycoerythrin, diphenyl-1-pyrenylphosphine (DPPP), and BODIPY® dyes (such as 4,4-difluoro-5-(4-phenyl-1,3-butadienyl-4-bora-3a,4a-diaza-s-indacene-3-undecanoic acid (BODIPY® 581/591) or (E,E)-3,5-bis-(4-phenyl-1,3-butadienyl)-4,4-difluoro-4-bora-3a,4a-diaza-s-indacene (BODIPY® 665/676)). Additional fluorescent indicator dyes include porphyrins, such as uroporphyrin I, uroporphyrin II, uroporphyrin III, and uroporphyrin IV; coproporphyrin I, coproporphyrin II, coproporphyrin III, and coproporphyrin IV; MS-tetraphenylporphyrin; deuteroporphyrin IX; hematoporphyrin IX; mesoporphyrin; and protoporphyrin IX; dihydrochloride.

Fluorescent indicator dyes which measure oxidative stress and which are capable of crossing the cell membrane include diacetate derivatives of fluorescent indicators. These derivatives can cross the cell membrane, where the acetates are cleaved by endogenous esterases. The resulting molecule is trapped inside the cell, where its fluorescence may be monitored. Examples of cell-permeable fluorescent indicator dyes include H2DCFDA, CM-H2DCFDA, HPF 4,5-diaminofluorescein diacetate, dihydroethidium, and DAF-FM diacetate.

In some embodiments, the Hb present in RBC becomes fluorescent upon exposure to ROS or RNS. Fluorescent heme degradation products form during the reaction of Hb with H2O2 (Nagababu et al, Free Radic. Biol. Med. 29:659-663, 2000). In particular embodiments, the endogenous Hb acts as the fluorescent indicator of oxidation, making it unnecessary to add an exogenous fluorescent indicator dye to the antioxidant activity assay.

In particular examples, the fluorescent indicator dye which measures oxidative stress is CM-H2DCFDA or DAF-FM. In another example, the endogenous Hb present in the RBC acts as the fluorescent indicator.

Free Radical Generators

In particular embodiments, a free radical generator is added to the RBC in the presence of the fluorescent indicator dye which measures oxidative stress following RBC lysis. The free radical generator creates ROS or RNS, which create oxidizing conditions. The oxidizing conditions are an "oxidative challenge" to the cell. In some examples, the free radical generator is added at a final concentration of about 0.01 mM to about 500 mM, such as about 0.1 mM to about 250 mM, about 1 mM to about 100 mM, about 5 mM to about 50 mM, or about 10 mM to 25 mM.

In particular examples, the free radical generator includes 2,2'-azobis(2,4-dimethylpentanenitrile), 2,2-azobis(2,4-dimethylpropanenitrile), 2,2'-azobis(2,4-dimethylbutanenitrile), 2,2'-azobis[2-(5-methyl-2-imidazolin-2-yl)propane]dihydrochloride, 2,2' azobis (2-amidinopropane)dihydrochloride (AAPH), 2,2'-azobis(2-amidinopropane)[2-(N-stearyl)amidinopropane]dihydrochloride (SA-1), 2,2'-azo(2-(2-imidazolin-2-yl)-propane)-[2-[2-(4-1-n-octyl)imidazolin-2-yl]-propane]dihydrochloride (C-8), 2,2'-azobis(4-methoxy-2,4-dimethylvaleronitrile) (MeO-AMVN), 2,2'-azobis(2,2'-azobis (2,4-dimethylvaleronitrile) (AMVN), azo-bis-isobutylnitrile, 2,2'-azobis (2-methylproprionate) (DAMP), and 2,2'-azobis-(2-amidinopropane). Additional free radical generators include hydrogen peroxide (H2O2), tert-butylhydroperoxide, cumene hydroperoxide, α-guanidinoglutaric acid, 3-morpholinosydnonimine (SIN-1), and hypoxanthine/xanthine oxidase. Serum or platelets can generate reactive nitrogen species.

In particular examples, the free radical generator is hydrogen peroxide or (H2O2), 2,2'-azobis-(2-amidinopropane) dihydrochloride (AAPH).

Samples

Disclosed herein are methods of determining the antioxidant activity of a test sample. A test sample includes at least one compound of interest which has potential antioxidant activity. In particular examples, the compound of interest includes a preparation which contains one or more purified compounds, for example vitamin C, vitamin E, gallic acid, glutathione, carotenes, lycopene, lutein, coenzyme Q, selenium, gallic acid, hyaluronic acid, MSM, phycocyanin, chlorophyll and derivatives, sugars, isolated milk peptides, xanthones, anthocyanins, and purified flavones and flavonoids (such as those from fruits and chocolate). In further examples, the compound of interest includes a combination of one or more purified compounds.

In additional embodiments, the test sample containing a compound of interest is a crude mixture, for example a food product, such as a juice, tea, or milk. In some examples, the compound of interest is present in a mixture of one or more food products, such as a mixture of teas, a mixture of tea and berry juice (for example green tea and berry extract), a mixture of fruit juices (such as orange juice with mango and kiwi juice), or a mixture of a fruit juice with a purified compound of interest (for example calcium-fortified juice or vitamin C-fortified juice). In some examples, the test sample is a food or beverage that is consumed by a subject, such as cooked food (for example, soups or stews), raw food (for example, egg products or raw egg fractions), baked goods (for example, breads, cookies, or granola bars), or meat or dairy products (raw or cooked); beverages, such as tea, soft drink, flavored water, milk or milk products, juice, or cocoa; or spices, such as cinnamon, cloves, cocoa powder, or dried herbs (such as oregano).

In additional examples, the test sample is a fungal culture or a culture media (such as liquid media or solid media, such as grain) inoculated with live fungal cells (such as yeast or mushroom), allowed to ferment under a specific set of conditions, and then dried. The end product contains both residual live fungal cells used in the fermentation, as well as metabolites or metabolic by-products produced by the cells.

In several embodiments, the test sample containing a compound of interest includes an extract. An extract is prepared from a material, such as a biological material (for example plant, animal, fungal, yeast or bacterial material). In some examples, the extract is prepared from a plant material, such as leaves (such as tea, for example green tea or black tea), bark, roots, stems, flowers, seeds (such as sunflower seed, grape seed, or flax seed), fruit (such as raspberries, blueberries, bilberries, Goji berries, Acai berries, grapes (or raisins), apples, Mangosteen, citrus fruits, bananas, or cherries), or vegetables (such as broccoli, carrots, or leafy greens). In some examples, fruit or vegetable can be fresh or dried, and the extract may be prepared from whole fruit or vegetable, or a portion thereof (such as skin, pulp, seeds, or combinations thereof). In additional examples, the extract is prepared from an animal material, such as meat, blood, tissue, cartilage, antlers, skin, hooves, eggs, egg shells, egg shell membranes, milk, or colostrum. In further examples, the extract is prepared from a fungus (for example, mushrooms (such as morel, shiitake, reishi, or chanterelle), *Penicillium paraherquei, Aspergillus niger*, or Cordyceps), yeast (for example, *Saccharomyces cerevisiae* or *S. carlsbergensis*), algae (such as *Chlorella, Fucus*, or kelp), cyanobacteria (such as Arthrospira platensis (spirulina), or Aphanizomenon flos-aquae), or bacteria (for example, *Bacillus cereus, Lactobacillus dextranicum, Micrococcus freudenreichii*, or *Sarcina lutea*).

In several embodiments the extract includes an aqueous extract. In one example, the extract is prepared by incubating a starting material with an aqueous solution, such as water or physiological saline (for example, normal saline, phosphate buffered saline, Hank's balanced salt solution, Ringer's solution, or lactated Ringer's solution) or combinations thereof. In a particular example, the aqueous extract is prepared by incubation in phosphate buffered saline (pH 7.2-7.4) for about 20 minutes at room temperature with gentle agitation.

In further embodiments, the extract includes an organic extract. In one example, the extract is prepared by incubating a starting material with at least one organic solvent. Solvents which may be used to prepare an organic extract include pentane, hexane, dichlorofluoromethane, chlorofluoromethane, dichloromethane, dimethylether, ethylmethylether, diethylether, methanol, ethanol, acetone, ethyl butyl ketone, dimethyl sulfoxide, glycerol, or mixtures thereof. In a particular example, the organic extract is prepared by dissolving the test sample in dimethyl sulfoxide, followed by dilution in PS containing 1% ethanol.

In additional examples, the extract is prepared using a combination of aqueous and organic solvents. For example, one or more organic solvents may be diluted in an aqueous solution (such as water or a buffer (such as PBS)). In particular examples, an extract is prepared by dissolving the test compound in a mixture of acetone and glycerol or a mixture of ethanol and glycerol. Acetone may be present at a final concentration of about 1% to about 80% (such as about 1%, about 2%, about 5%, about 10%, about 20%, about 40%, about 50%, about 70%, or about 80%). Ethanol may be present at a final concentration of about 1% to about 80% (such as about 1%, about 2%, about 5%, about 10%, about 20%, about 40%, about 50%, about 70%, or about 80%). Glycerol may be present at a final concentration of about 1% to about 80% (such as about 1%, about 2%, about 5%, about 10%, about 20%, about 40%, about 50%, about 70%, or about 80%). Combinations of acetone, ethanol, or glycerol may be used to prepare an extract. In specific examples, the mixture is 20% acetone and 5% glycerol in PBS or 20% ethanol and 5% glycerol in PBS.

In some examples, the extract is further treated to remove protein, for example by precipitation using ammonium sulfate, followed by filtration and/or centrifugation. In some examples, the extract is filtered through a cellulose acetate, nylon, polypropylene, or Teflon® filter. In a particular example, the extract is sterilized, for example by filtration, such as filtration through a 0.2 µm cellulose acetate filter. In a further example, the aqueous or organic extract may be diluted in a physiological buffer such that the solvent concentration is non-toxic to intact cells. In particular examples, the extract is diluted in isotonic buffer such as phosphate buffered saline (pH 7.2-7.4) or Hank's balanced salt solution, for example using serial five-fold dilutions In several embodiments, the test sample containing the compound of interest is serum or plasma from a subject. In a particular example, the subject is one which has consumed an extract or a compound of interest. In some examples, the subject who has ingested the test sample or compound of interest does not have an underlying disease (such as cardiovascular disease (for example atherosclerosis, ischemia/reperfusion injury, restenosis, and hypertension), cancer, inflammatory diseases (such as acute respiratory distress syndrome, asthma, inflammatory bowel disease, dermal and ocular inflammation, and arthritis), metabolic disease such as diabetes, and diseases of the central nervous system such as amyotrophic lateral sclerosis, Alzheimer disease, Parkinson disease, or stroke). In one example, a fasting subject has provided a baseline blood sample, and then has consumed the extract or compound of interest within at least about 5 minutes to about 24 hours of drawing a blood sample for preparation of serum or plasma, such as within about 10 minutes to about 20 hours, about 30 minutes to about 18 hours, about one hour to about 16 hours, about 2 hours to about 12 hours, or about 4 hours to about 8 hours. In a particular example, blood samples are collected immediately before and 1, 2, and 4 hours after consuming a test sample containing a compound of interest. In some examples, the subject of interest has consumed the extract or compound of interest in a single dose. In another example, the subject has consumed the extract or compound of interest in multiple doses, for example every other day, once per day, twice per day, three times per day or four times per day. In examples wherein the subject has consumed a compound of interest in multiple doses, the serum or plasma is prepared before and at intervals after consumption of the compound of interest. For example the compound of interest may be consumed for about 3 days to about 12 weeks, such as about 5 days to 10 weeks, about one week to about eight weeks, or about two weeks to about four weeks.

In additional embodiments, the antioxidant activity of a test sample, such as an extract or a compound of interest, may be compared with a standard with known antioxidant activity to determine relative antioxidant activity of the test sample. Examples of standards include gallic acid, TROLOX® (6-hydroxy-2,5,7,8-tetramethylchroman-2-carboxylic acid, a water soluble analog of vitamin E), ascorbic acid, grape seed extract, and MSM. In particular embodiments, the standard is gallic acid, TROLOX®, or MSM.

The present disclosure is illustrated by the following non-limiting Examples.

EXAMPLES

Example 1

Extraction of Antioxidants from Natural Products

This example describes methods for extracting antioxidants from natural products using aqueous or organic solvents.

Biological materials were extracted in an aqueous solvent. Water-soluble compounds were extracted from dried cyanobacteria. Extraction was carried out in phosphate-buffered saline (PBS) at a concentration of 100 mg of starting material per ml of PBS for 20 minutes at room temperature with constant rocking. Solids were precipitated by centrifugation for 10 minutes at 400×g. The supernatant was filtered through a 0.2 µm cellulose-acetate syringe filter. Serial five-fold dilutions of the extract in PBS were used in the antioxidant activity assay.

Test products were also extracted in an organic solvent. The extract was made by dissolving a test product in pure anhydrous dimethyl sulfoxide. Serial five-fold dilutions were made in PBS containing 1% ethanol for use in the antioxidant activity assay.

Another test product extract was made by dissolving a test product in methanol. Serial dilutions were made in PBS for use in the antioxidant activity assay. An additional extract was made by dissolving a test product in 50:50 v/v acetone/water for one hour with constant shaking. Serial dilutions were made in PBS for use in the antioxidant activity assay.

Example 2

Rapid Assay of Antioxidant Activity in Red Blood Cells (CAP-e Assay)

This example describes a method for rapid assessment of antioxidant activity of a test sample using intact red blood cells which are lysed following treatment with a test sample (CAP-e assay).

Methods

Whole blood was collected from healthy volunteers. A double density gradient was prepared, where 3 ml of HISTOPAQUE® 1099 was overlaid with 3 ml of HISTOPAQUE® 1077. 5-6 ml of whole anticoagulated blood was layered on top of the double gradient and centrifuged for 25 minutes at 2400 rpm. The plasma, peripheral blood mononuclear cells, polymorphonuclear cells, and HISTOPAQUE® were removed using a transfer pipette. The remaining packed red blood cell fraction was washed three times in 10-14 ml PBS by centrifugation at 2400 rpm for 10 minutes. After the third wash the supernatant was removed, and the packed RBC were aliquoted for storage by pipetting 200 µl packed RBC into 10 ml PBS. The RBC aliquots were stored at 4-8° C. until use. The cells were used the same day or after up to 120 days of storage. For most routine testing, the RBC were typically prepared 2-4 weeks before use.

The antioxidant standard gallic acid (GA) was prepared by dissolving 85 mg of GA in 0.5 ml of 99.95% methanol. 0.2 ml of the dissolved GA was immediately diluted in 49.8 ml of PBS. Serial five-fold dilutions of the GA solution were prepared in PBS.

The serial dilutions of the extract and the GA standard were aliquoted in duplicate in a deep-well microplate. 100 µl of the RBC suspension was added to each well. The plate was incubated for 20 minutes at room temperature in the dark. Unabsorbed antioxidants were removed by washing the RBC three times in PBS by centrifugation for 2.5 minutes at 2400 rpm. The RBC pellets were lysed by incubation in 0.08 ml distilled water for 5 minutes at room temperature.

The fluorescent probe was prepared by reconstituting 50 µg CM-H2DCFDA in 0.2 ml anhydrous dimethyl sulfoxide, which was then added to 7.5 ml PS. After lysis of RBC was complete 70 µl of the lysed RBC were transferred to a black microplate and 50 µl of CM-H2DCFDA was added to each well (16.25 µM CM-H2DCFDA). The microplate was incubated for 20 minutes at room temperature or 37° C. in the dark. Then 50 µl H2O2 (0.0004% final concentration) or 50 µl AAPH (1 mg/ml final concentration) was added to each well. Wells exposed to H2O2 were incubated for 5 minutes at room temperature in the dark. Wells exposed to AAPH were incubated for one hour at room temperature or 37° C. in the dark. Fluorescence intensity was measured in a Tecan Spectrafluor fluorescence plate reader with excitation at 485 nm and emission at 535 nm.

Negative controls were RBC which were not treated with a test sample or standard and were not exposed to an oxidative challenge. Positive controls were RBC which were not treated with a test sample or standard, but were exposed to an oxidative challenge. The percent inhibition of oxidative damage was calculated as [(fluorescence intensity of RBC treated with free radical generator−fluorescence intensity of RBC treated with test sample and free radical generator)/(fluorescence intensity of RBC treated with free radical generator−fluorescence intensity of untreated RBC)]×100.

Results

Figure 2A:
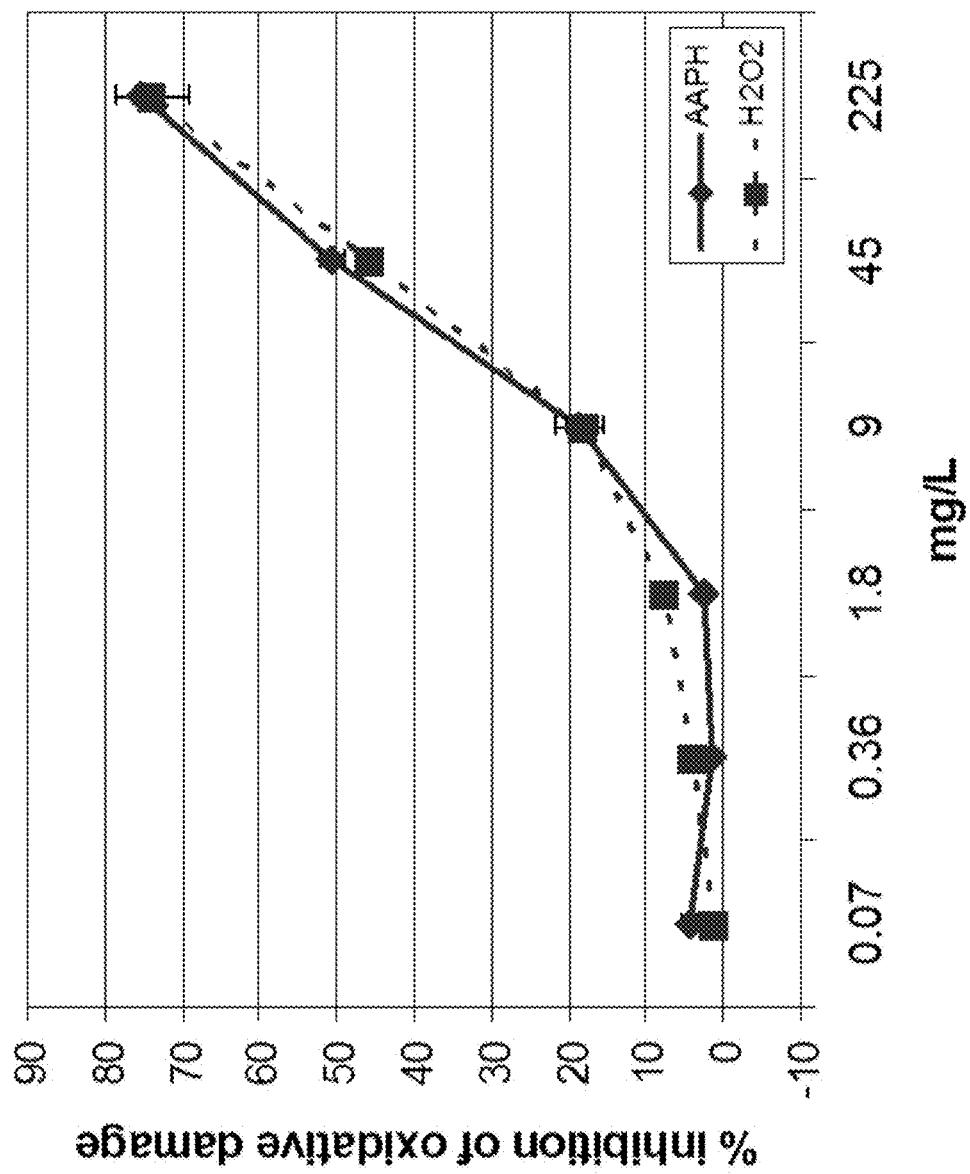
FIG. 2 is a series of graphs showing dose response curves for inhibition of oxidative damage in RBC by the standards gallic acid (FIG. 2A) and TROLOX® (FIG. 2B). Oxidative challenge was created using the hydroxyl free radical generator $H_2O_2$ or the peroxyl free radical generator AAPH.
Figure 2B:
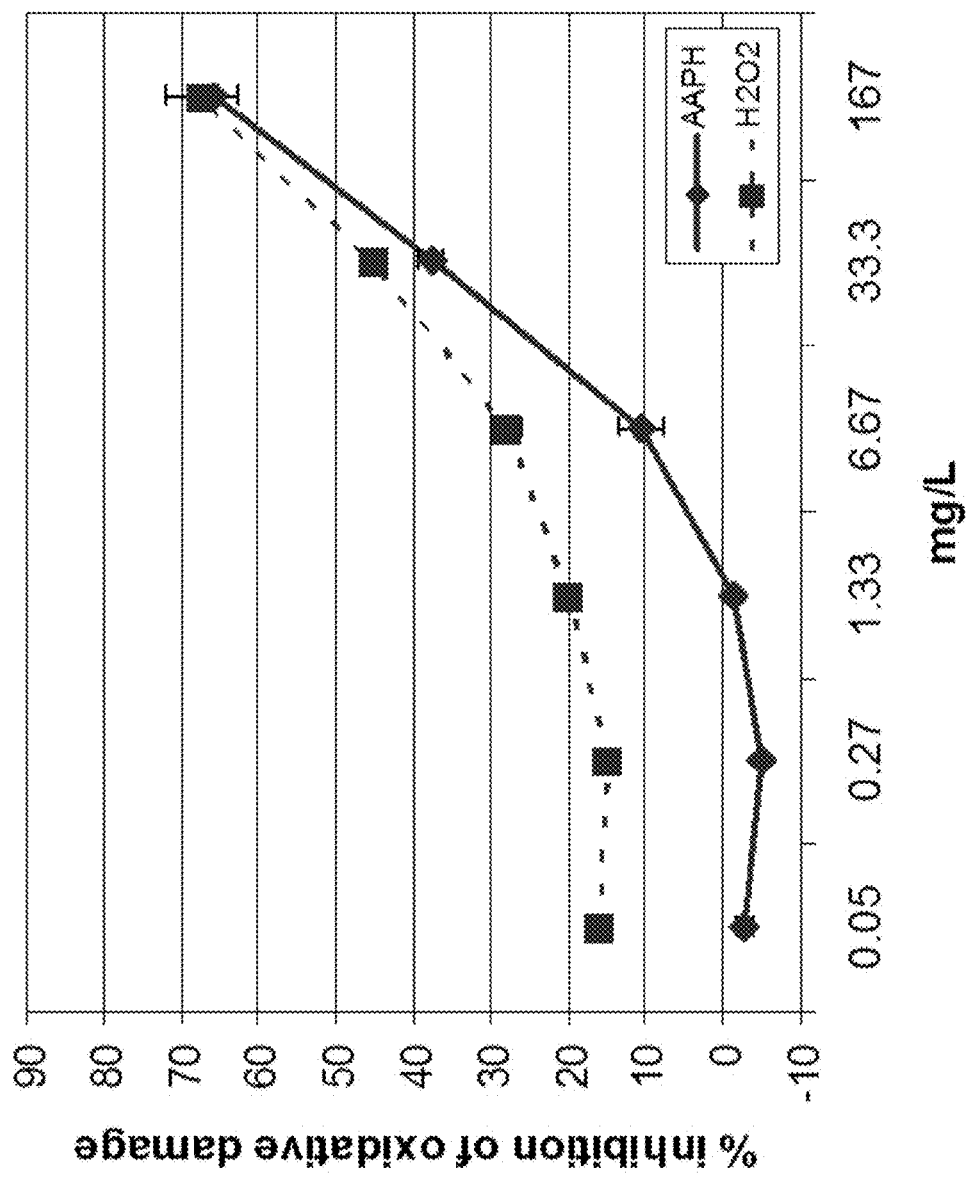

Standard curves were generated for the antioxidant standards gallic acid (GA) and TROLOX®. In the CAP-e assay, GA was equally effective at inhibiting oxidative damage caused by the hydroxyl free radical generator H2O2 and the peroxyl free radical generator AAPH at all concentrations (FIG. 2A). TROLOX® protected RBC from damage from both free radical generators at higher concentrations, but was more effective against hydroxyl free radicals at lower concentrations (FIG. 2B).

Figures 3A, 3B:
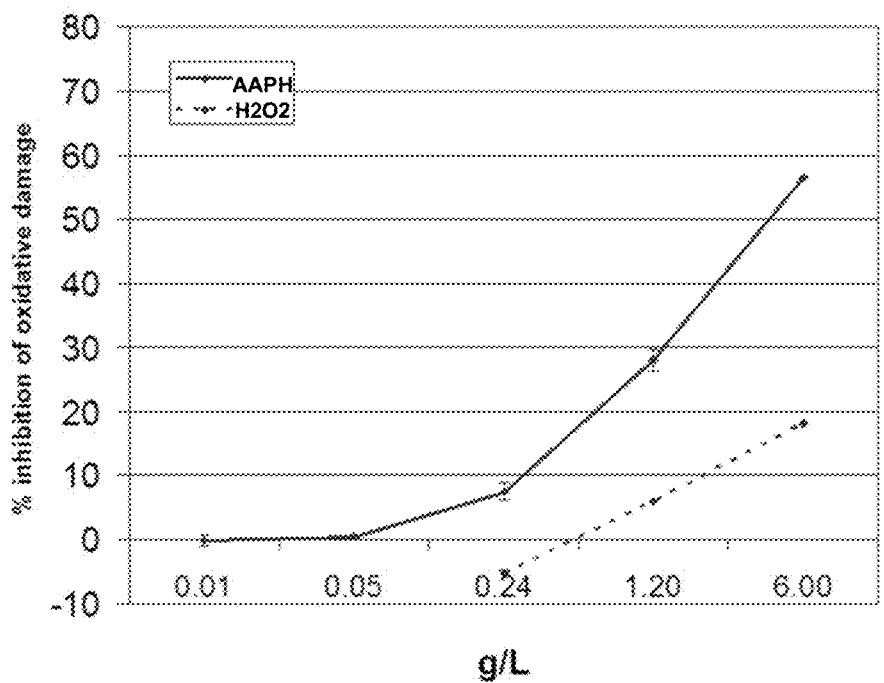
FIG. 3 is a series of graphs showing the percent inhibition of oxidative damage resulting from treatment of RBC with increasing concentrations of an anthocyanin-rich berry product (FIG. 3A) or a milk-based extract (FIG. 3B). Oxidative damage was induced by the free radical generators $H_2O_2$ or AAPH.

The CAP-e assay was used to assess the ability of various test products to protect intact RBC from oxidative damage. FIG. 3 illustrates the dose response curves for an anthocyanin-rich berry product and a milk-based extract. The anthocyanin-rich product provided greater protection from peroxyl radicals generated by AAPH than from hydroxyl radicals generated by H2O2 (FIG. 3A). Similarly, the milk-based extract also showed greater protection from peroxyl radical damage than hydroxyl radical damage (FIG. 3B).

Example 3

Calculation of the CAP-e Value

This example describes the method for calculating the CAP-e value of a sample and provides exemplary CAP-e values for several foods.

The CAP-e value of a given test product is based on the comparison of the dose-response of inhibition of oxidative damage between the standard gallic acid (GA) and the test sample. For each test sample or compound, the IC50 for inhibition of oxidative damage is calculated. The IC50 for GA was 0.032 g/l, determined from more than 60 independent experiments. The CAP-e units of GA was set as 1,000 Gallic Acid Equivalents (GAE). For calculating the CAP-e units of a test sample, the IC50 for the test sample was divided by the IC50 for GA, and multiplied by the CAP-e value for GA (1,000). The CAP-e value was expressed as CAP-e units/g of sample.

Figure 4:
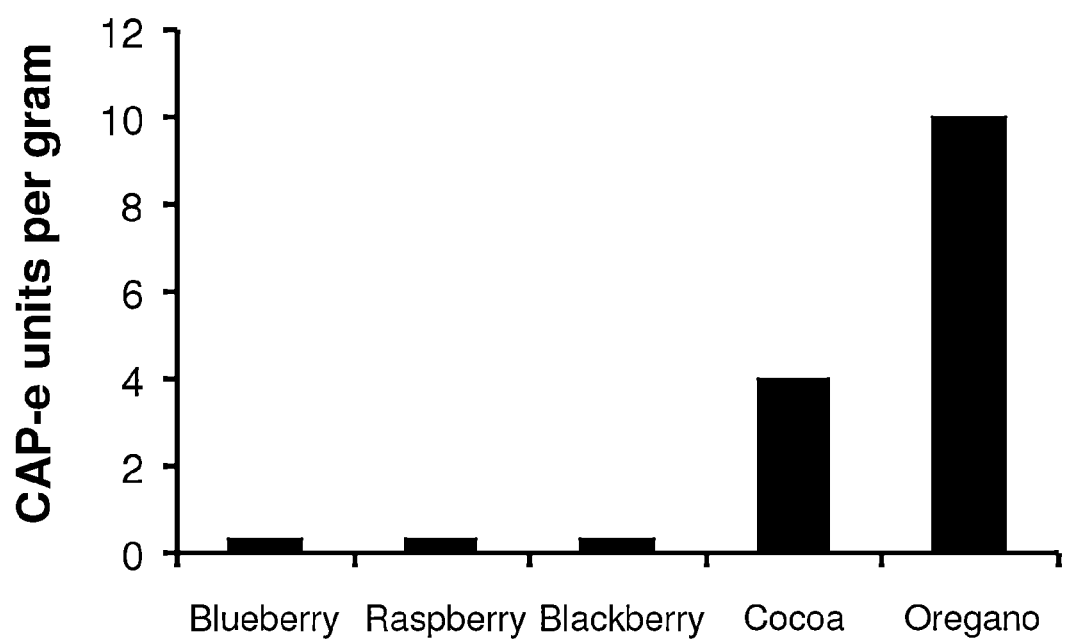
FIG. 4 is a graph showing CAP-e units per gram for some common foods.

Extracts of blueberry, raspberry, blackberry, cocoa, and oregano were prepared essentially as described in Example 1. 0.5 g of each food was extracted in 5 ml of saline. Antioxidant activity was determined as described in Example 2. The RBC were prepared and stored at 4° C. prior to the experiment, rather than being freshly prepared. The CAP-e values are shown in FIG. 4.

Example 4

Comparison of Antioxidant Activity of Extracts Prepared with Aqueous or Organic Compounds This example describes a comparison of CAP-e values of extracts prepared with aqueous or organic compounds.

Methods

Extracts of a culinary spice (for example, cloves) were prepared essentially as described in Example 1. Four different extracts of the spice were prepared by using the following solvents: 1) PBS, 2) 20% acetone in PBS, 3) 5% glycerol in PBS, and 4) a mixture of 20% acetone and 5% glycerol in PBS. The extracts were prepared essentially as described in Example 1, except the supernatant obtained following centrifugation was not filtered. RBC were prepared as described in Example 2. The CAP-e assay was performed as described in Example 2 and the CAP-e value was calculated as described in Example 3.

Results

Figure 5:
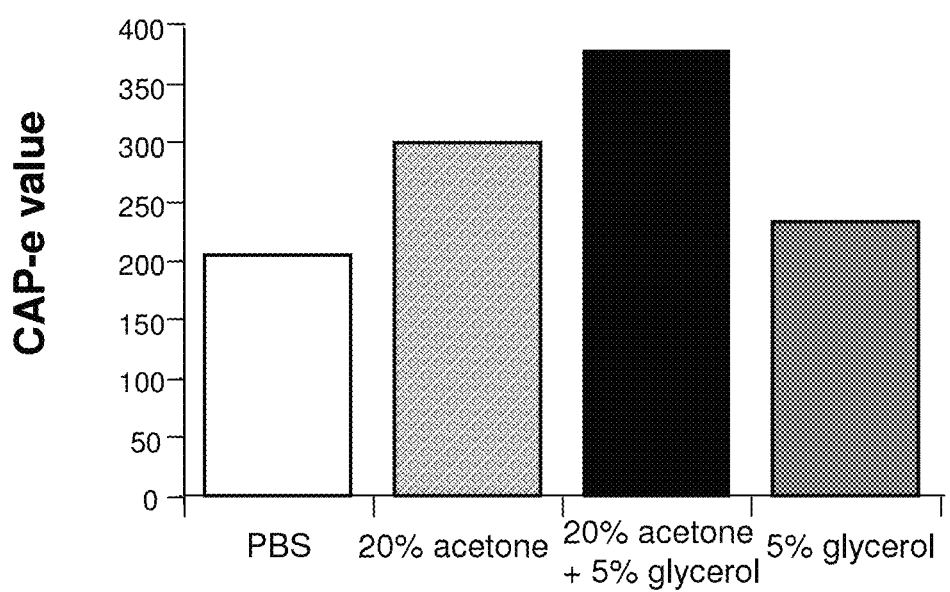
FIG. 5 is a graph showing the CAP-e value of extracts of a culinary spice prepared using different solvents for the extraction.

The CAP-e value for extracts of a culinary spice prepared using different solvents was determined using RBC. FIG. 5 shows the CAP-e values of the different extracts. The antioxidant activity of the extract in PBS reflects water-soluble antioxidants. The increased antioxidant activity of the extract in either acetone or glycerol in PBS reflects water-soluble antioxidants and some lipid-soluble antioxidants. The antioxidant activity of the extract in the mixture of acetone and glycerol in PBS reflects a combination of water-soluble and lipid-soluble antioxidants. Since the mixture of acetone and glycerol provided the extract with the highest antioxidant activity it can be concluded that acetone and glycerol each contribute to extraction of lipid-soluble antioxidant compounds from the test product.

Example 5

Comparison of Microplate-Based and Flow Cytometry CAP Methods

This example compares the CAP-e assay method in which RBC are lysed following exposure to test compounds to CAP assay methods which maintain intact cells throughout the duration of the assay.

Methods

The CAP-e assay was performed as described in Example 2. For purposes of comparison, the CAP assay was also performed under conditions in which the RBC remain intact throughout the duration of the assay. Briefly, RBC were prepared as described in Example 2. The RBC were incubated for 1.5 hours at room temperature with a test sample, followed by two washes in PS at 2400 rpm for 2.5 minutes. In some experiments, the RBC were lysed as described in Example 2. In other experiments, the RBC were not lysed. RBC (lysed or unlysed) were incubated with 16.25 $\mu$M CM-H2DCFDA for 1 hour at 37° C. Unabsorbed CM-H2DCFDA was removed by two washes in PS at 2400 rpm for 2.5 minutes. The RBC were incubated with 167 mM H2O2 for 45 minutes to induce oxidative stress, then washed twice in PBS and transferred to vials on ice. CM-H2DCFDA fluorescence intensity was analyzed by flow cytometry (flow cytometry assay). Alternatively, RBC were kept in the assay plate and fluorescence intensity was analyzed by a microplate reader (whole cell CAP assay and CAP-e assay).

Results

Figure 6:
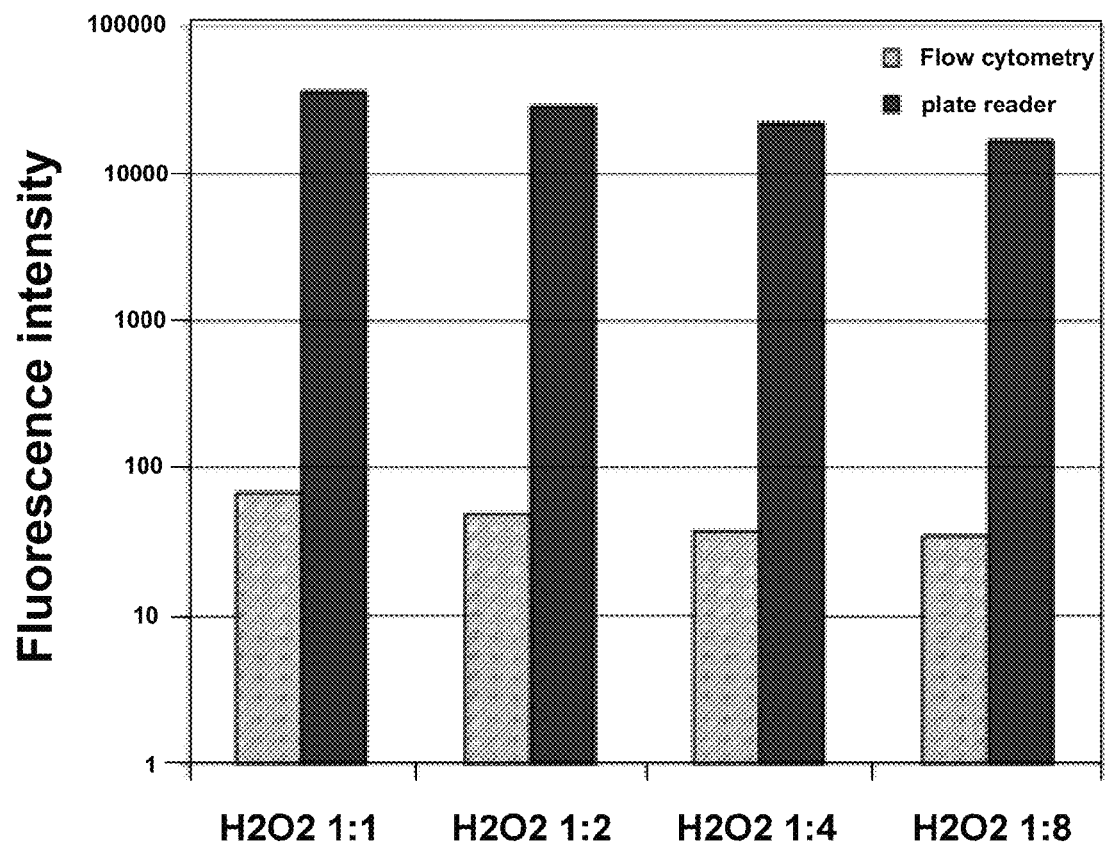
FIG. 6 is a graph comparing fluorescence intensity in RBC exposed to decreasing concentrations of $H_2O_2$ plotted on a logarithmic scale. $H_2O_2$ was used at a starting concentration of 167 mM (1:1), then serial two-fold dilutions were made (1:2, 1:4, and 1:8). Shaded bars indicate fluorescence intensity in RBC measured by flow cytometry assay. Solid bars indicate fluorescence intensity measured by the whole cell CAP assay (plate reader).

Fluorescence intensity in response to the hydroxyl radical generator H2O2 was compared in the whole cell CAP assay and the flow cytometry assay. The fluorescence intensity generated by all concentrations of H2O2 tested was more than two orders of magnitude greater in the whole cell CAP assay than in the flow cytometry assay (FIG. 6).

Figure 7A:
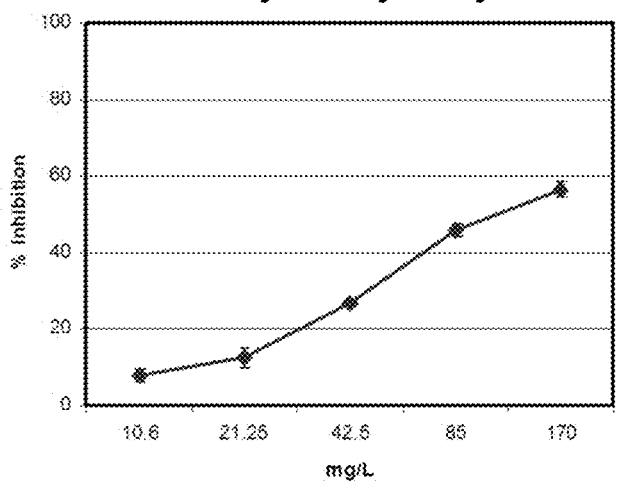
FIG. 7A shows the dose response curve measured by the flow cytometry assay.
Figure 7B:
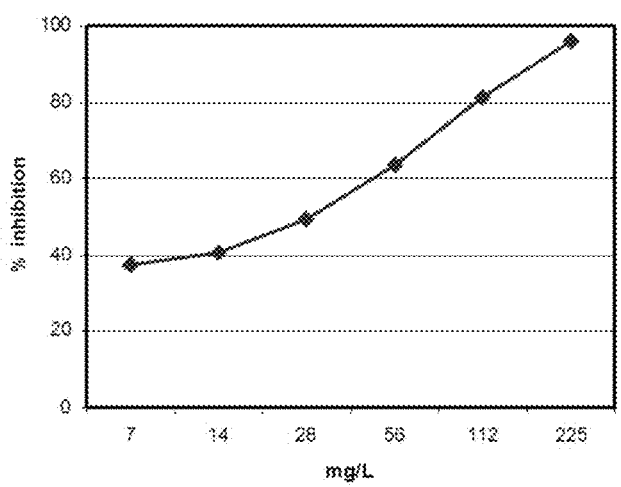
FIG. 7B shows the dose response curve measured by the whole cell CAP assay.
Figure 7C:
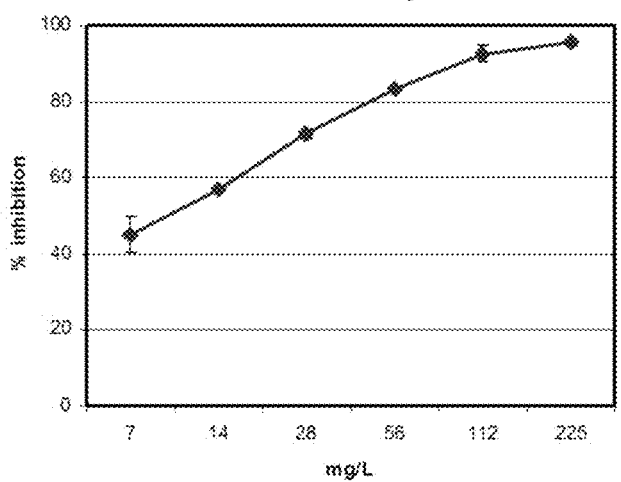
FIG. 7C shows the dose response curve measured by the CAP-e assay.

Standard curves were generated using GA as the antioxidant standard for each method (FIG. 7). This comparison showed that the CAP-e assay had the advantage of higher sensitivity and gave the most linear standard curve compared with the other methods tested. The CAP-e method shows a greater inhibition of oxidative damage by the standard at all concentrations than the flow cytometry assay (FIGS. 7A and 7C). The sensitivity of the CAP-e assay was similar to that of the whole cell CAP assay, however the CAP-e assay generated a more linear standard curve (FIGS. 7B and 7C).

Figure 8A:
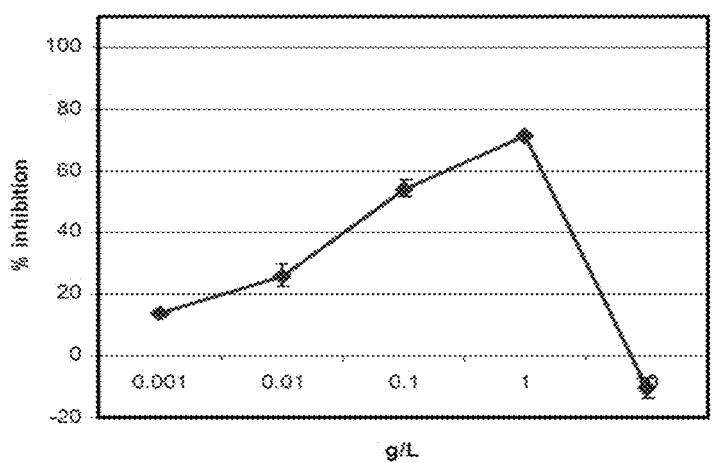
FIG. 8A shows the dose response curve measured by the flow cytometry assay.
Figure 8B:
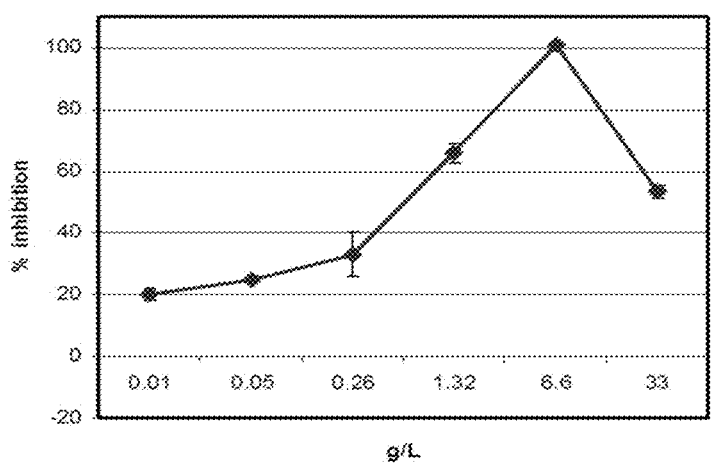
FIG. 8B shows the dose response curve measured by the whole cell CAP assay.
Figure 8C:
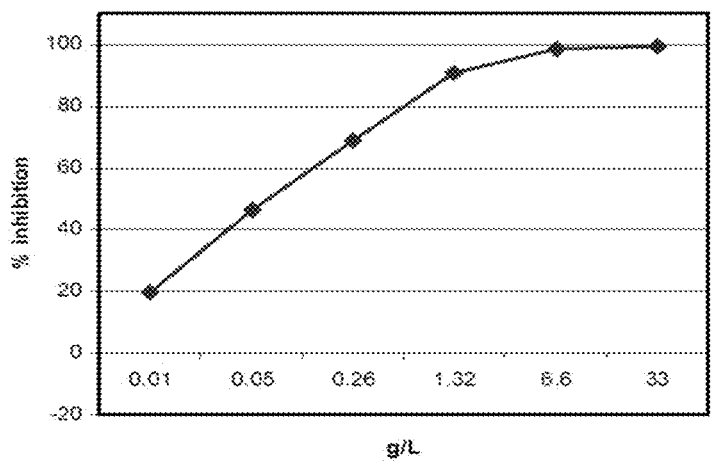
FIG. 8C shows the dose response curve measured by the CAP-e assay.

The inhibition of oxidative damage by a test sample was assessed by measurement of fluorescence intensity in RBC by the flow cytometry assay, the whole cell CAP assay, or the CAP-e assay (FIGS. 8 and 9). The inhibition of oxidative damage by a test sample containing hyaluronic acid and MSM could not be detected by the flow cytometry assay at concentrations over 1 g/l (FIG. 8A). Inhibition of oxidative damage by the same compound began to decrease at concentrations above 6.6 g/l in the whole cell CAP assay (FIG. 8B). However, no interference was observed in the CAP-e assay, even at concentrations of 33 g/l.

Figure 9A:
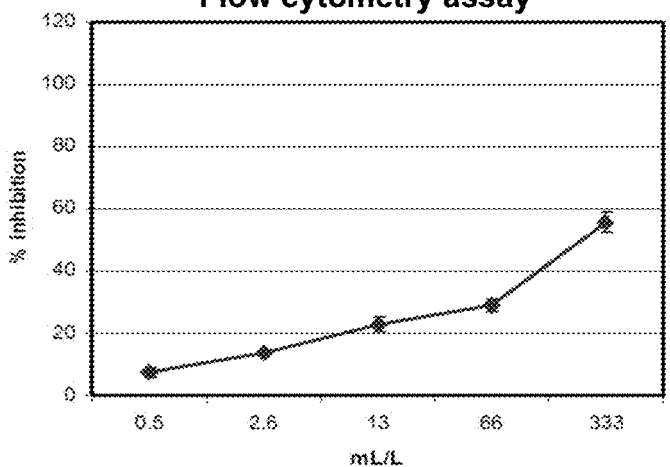
FIG. 9A shows the dose response curve measured by the flow cytometry assay.
Figure 9B:
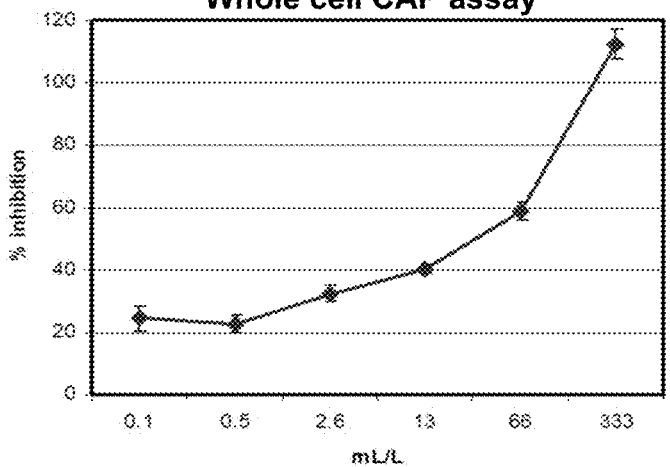
FIG. 9B shows the dose response curve measured by the whole cell CAP assay.
Figure 9C:
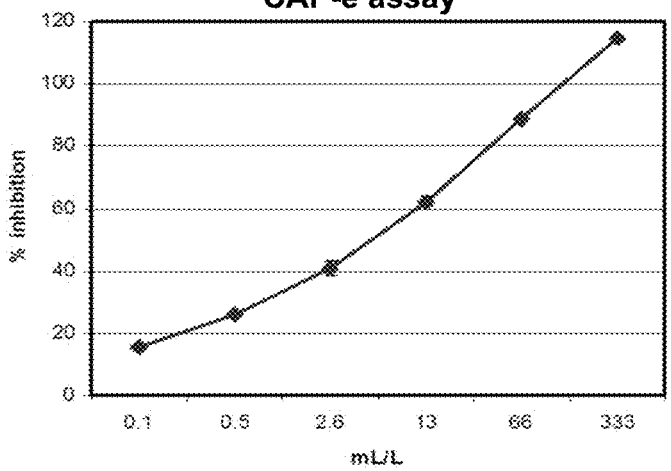
FIG. 9C shows the dose response curve measured by the CAP-e assay.

Inhibition of oxidative damage by a fruit juice was also tested using the three assay methods (FIG. 9). A maximum inhibition of 55% was measured by the flow cytometry assay (FIG. 9A). However, the whole cell CAP assay an the CAP-e assay were able to demonstrate inhibition of greater than 100% at the highest concentration, indicating that the RBC were more protected from oxidative damage than the negative control cells which were not exposed to a free radical generator (FIGS. 9B and 9C). The CAP-e assay demonstrated a more linear dose response curve for this test sample than the whole cell CAP assay (FIGS. 9B and 9C).

Example 6

CAP-e Assay Using Hemoglobin as a Fluorescent Indicator of Oxidative Damage

This example describes a modification of the CAP-e assay in which the endogenous hemoglobin (Hb) of the RBC acts as the fluorescent indicator of oxidative damage.

The CAP-e assay was performed essentially described in Example 2, except that there was no addition of a fluorescent indicator dye to the lysed RBC. Instead, the fluorescence of the endogenous Hb of the RBC in response to oxidative damage was determined.

Figure 10:
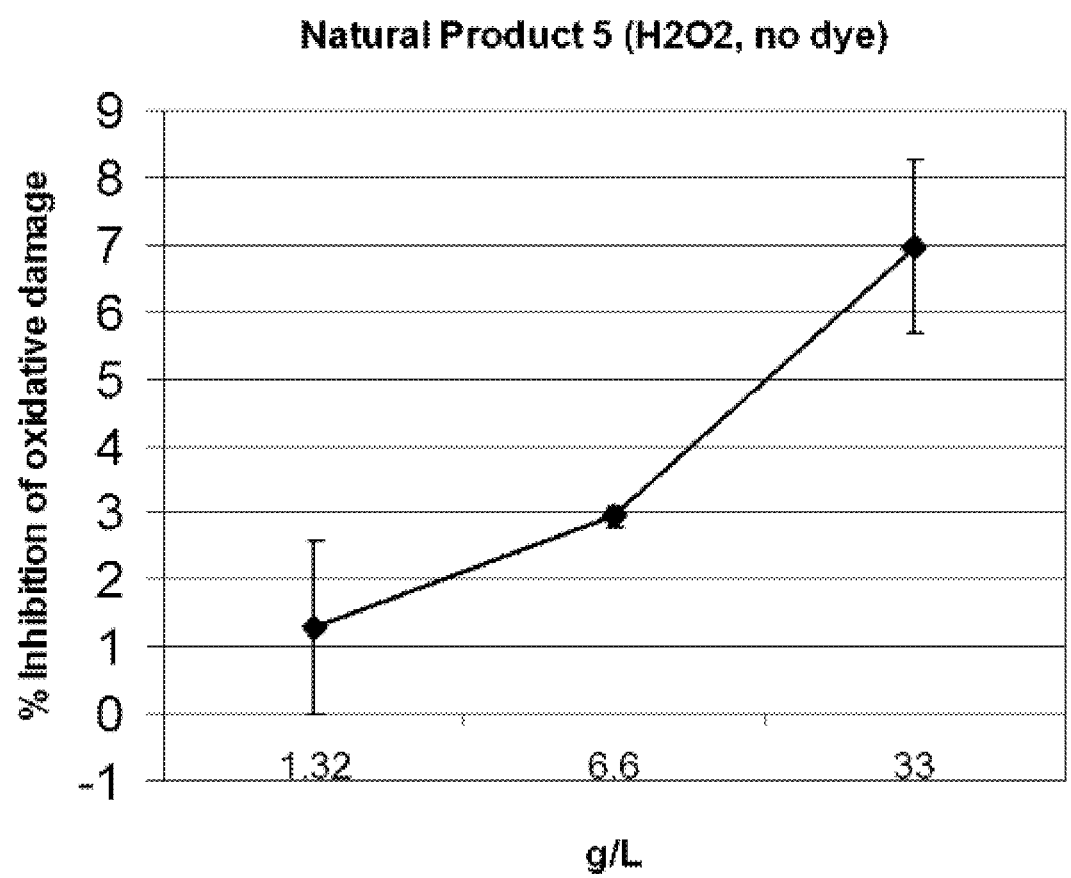
FIG. 10 is a graph showing the percent inhibition of oxidative damage in the CAP-e assay when hemoglobin is used as the fluorescent indicator of oxidative damage. RBC were treated with a test sample, lysed, and percent inhibition of oxidative damage generated by H2O2 was measured.

FIG. 10 shows the inhibition of oxidative damage by a test compound in RBC using the modified CAP-e assay. Increasing concentrations of the test compound were added to the RBC and oxidative challenge was generated using H2O2. Fluorescence intensity was measured as described in Example 2.

Example 7

Measurement of Antioxidant Protection in RBC from Subjects

This example describes use of RBC from subjects in the CAP-e assay to measure antioxidant protection.

Figure 11:
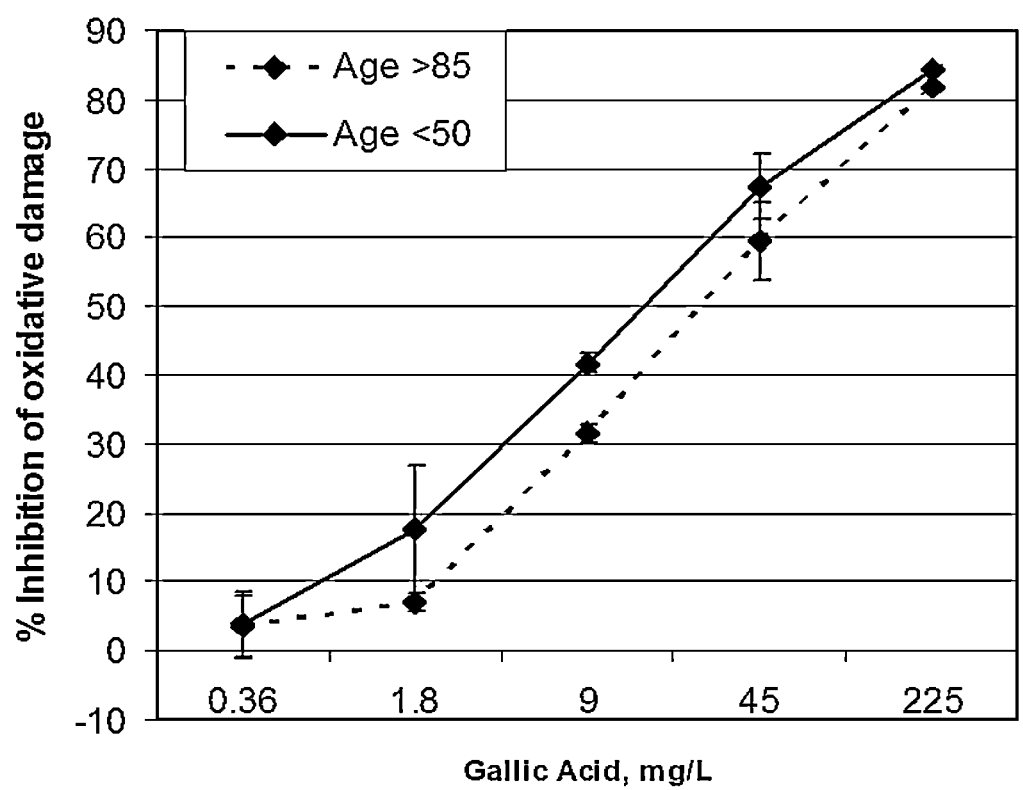
FIG. 11 is a graph of a dose response curve for GA, showing percent inhibition of oxidative damage generated by H2O2 in RBC from a subject under 50 years of age (solid line) and RBC from a subject over 85 years of age (dotted line).

The CAP-e assay was performed essentially as described in Example 2. RBC were obtained from a person under 50 years of age and a person over 85 years of age. The inhibition of oxidative damage by increasing concentrations of GA was measured by determining the fluorescence intensity of CM-H2DCFDA in the presence of the free radical generator H2O2 (FIG. 11). More GA was required to provide the same level of protection from antioxidant damage for the RBC from the older person than for the RBC from the younger person.

Example 8

Testing of Antioxidant Activity of Serum Samples from Subjects

This example describes testing of antioxidant activity of serum from subjects which have ingested an extract or compound of interest.

Serum is prepared from subjects who have ingested an extract or compound of interest. A baseline blood sample is drawn from fasting subjects. The subjects consume 10 g of Goji berries. Blood samples are drawn 30 minutes, 1 hour, 2 hours, and 4 hours after consumption of the test product. The assay is performed essentially as described in Example 2, except the test sample is replaced by crude serum from the subject with a final dilution of 1:3 in PS in the test plate.

Serum is prepared from subjects from a baseline blood sample, and blood samples drawn 10 minutes, 30 minutes, 1 hour, and 2 hours after ingesting 1 g vitamin C. The assay is performed essentially as described in Example 2, except the test sample is replaced by crude serum from the subject with a final dilution of 1:3 in PS in the test plate.

Serum is prepared from subjects participating in a placebo-controlled trial. Subjects consume vitamin C, enhanced vitamin C with increased bioavailability, or a placebo. Blood is collected before consumption, and 30 minutes, 1 hour, 2 hours, and 4 hours after ingesting a single dose of the test sample. Blood is also collected from subjects after 7 days, 14 days, and 28 days of daily consumption of the test sample. The assay is performed essentially as described in Example 2, except the test sample is replaced by crude serum from the subject with a final dilution of 1:3 in PS in the test plate.

A cross-over design study is also used. Subjects are tested on two separate days which are two weeks apart. On one day, the subject will receive a placebo and on the other day the subject will receive 2 g of an extract from blue-green algae. Blood is collected prior to consumption of the test sample and 1 hour and 2 hours after consumption of the test sample. The assay is performed essentially as described in Example 2, except the test sample is replaced by crude serum from the subject with a final dilution of 1:3 in PS in the test plate.

Example 9

In Vivo Antioxidant Activity of a Juice Blend

This example describes measurement of antioxidant activity in serum samples from subjects who consumed a juice blend.

Methods

Twelve volunteer subjects age 19-52 participated in the study. Volunteers were scheduled for two study days at least one week apart. A baseline blood sample was drawn from each subject at the start of the study day. Immediately after collection of the baseline sample, 120 ml of the juice blend (MonaVie Active) or a placebo was provided for consumption. Blood samples were subsequently drawn at 1 and 2 h after ingestion of the test sample. At each time point, 6 ml of blood was drawn into serum separator vials. The vials were placed at room temperature for 30 min to allow for complete coagulation. The vials were centrifuged at 400×g for 10 min, and the serum was pipetted into multiple aliquots, which were frozen for later testing of antioxidant status. The serum antioxidant status was assessed using the CAP-e assay as described in Example 2.

Figure 12:
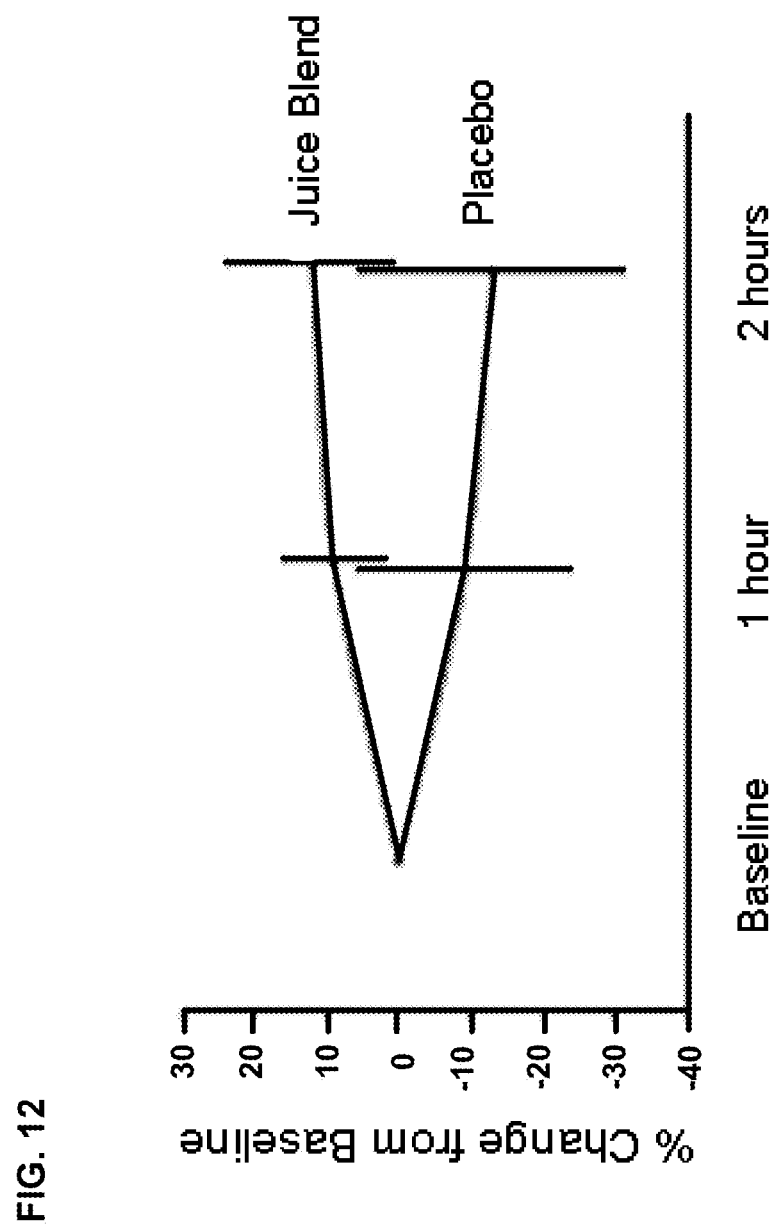
FIG. 12 is a graph showing change in CAP-e value compared to baseline in serum samples from subjects after consumption of a juice blend or a placebo (average±standard deviation; n=12).

Consumption of the juice blend resulted in an increase in the serum antioxidant capacity within 2 h of consumption in 11 of 12 study participants. The antioxidant capacity was tested using the CAP-e assay for serum samples obtained at baseline and at 1 and 2 h post-consumption (FIG. 12). The increase in serum antioxidant capacity was statistically significant both at 1 h ($p<0.027$) and at 2 h ($p<0.015$) post-consumption. When a paired t test was performed on the normalized data from each person's response to placebo versus juice blend, the significance at 2 h post-consumption was even stronger ($p<0.01$).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method for determining antioxidant activity of a sample in red blood cells, the method comprising:
   adding a sample to intact red blood cells under conditions which permit the sample to cross the cell membrane of the intact red blood cells;
   washing the red blood cells to remove sample which has not crossed the cell membrane of the red blood cells;
   lysing the washed red blood cells;
   inducing oxidative stress in the lysed red blood cells; and
   detecting fluorescence intensity from a fluorescent indicator which exhibits oxidation-sensitive changes in fluorescence intensity in the lysed red blood cells,
wherein a decrease in fluorescence intensity in the lysed red blood cells in the presence of the sample as compared to a control comprising red blood cells which have not been treated with the sample or red blood cells treated with a standard with known antioxidant activity indicates the antioxidant activity of the sample.

2. The method of claim 1, wherein lysing the red blood cells comprises exposing the red blood cells to hypotonic conditions, detergent, or physical disruption.

3. The method of claim 1, wherein the fluorescent indicator is hemoglobin in the red blood cells.

4. The method of claim 1, further comprising adding an exogenous fluorescent indicator to the intact red blood cells.

5. The method of claim 4, wherein the exogenous fluorescent indicator comprises 5-(and-6-)-chloromethyl-2',7'-dichlorodihydrofluorescein diacetate acetyl ester (CM-H2DCFDA) or 4-amino-5-methylamino-2',7'-difluorofluorescein (DAF-FM) diacetate.

6. The method of claim 1, wherein inducing oxidative stress comprises adding a free radical generator to the lysed red blood cells.

7. The method of claim 6, wherein the free radical generator comprises hydrogen peroxide, tert-butylhydroperoxide, cumene hydroperoxide, or 2,2'-azobis(2-amidinopropane) dihydrochloride (AAPH).

8. The method of claim 1, wherein detecting fluorescence intensity in the lysed red blood cells comprises detecting fluorescence intensity using a microplate reader.

9. The method of claim 1, wherein the sample comprises an extract.

10. The method of claim 9, wherein the extract comprises an aqueous extract, an organic extract, or a combination thereof.

11. The method of claim 10, further comprising dilution of the extract in a physiological buffer.

12. The method of claim 1, wherein the sample is serum or plasma from a subject.

13. The method of claim 12, wherein the subject has consumed a compound of interest.

14. The method of claim 1, wherein the sample comprises a plurality of standards with known antioxidant activity.

15. The method of claim 14, wherein the plurality of standards comprises one to six standards.

16. The method of claim 1, wherein the sample comprises a compound of interest.

17. The method of claim 1, wherein adding the sample to the intact red blood cells comprises administering the sample to a subject.

* * * * *